United States Patent
Momoda et al.

(10) Patent No.: US 7,521,004 B2
(45) Date of Patent: Apr. 21, 2009

(54) CHROMENE COMPOUND

(75) Inventors: Junji Momoda, Shunan (JP); Yuichiro Kawabata, Shunan (JP); Nobuyuki Tanaka, Shunan (JP); Arihiro Iwata, Shunan (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 10/572,098

(22) PCT Filed: Sep. 14, 2004

(86) PCT No.: PCT/JP2004/013712

§ 371 (c)(1),
(2), (4) Date: Jan. 3, 2007

(87) PCT Pub. No.: WO2005/028465

PCT Pub. Date: Mar. 31, 2005

(65) Prior Publication Data

US 2007/0215844 A1    Sep. 20, 2007

(30) Foreign Application Priority Data

Sep. 18, 2003    (JP) .............................. 2003-325681

(51) Int. Cl.
*F21V 9/00*    (2006.01)
*G02B 5/02*    (2006.01)
*G02C 7/10*    (2006.01)
*G02F 1/361*    (2006.01)
*G03B 11/00*    (2006.01)

(52) U.S. Cl. ...................... 252/582; 549/381; 549/344; 549/331; 549/345; 524/110; 523/106

(58) Field of Classification Search ......... 252/582–589; 428/412, 424.2, 441–442, 461–463, 500–523; 549/381

See application file for complete search history.

(56) References Cited

U.S. PATENT DOCUMENTS

| 5,645,767 | A | 7/1997 | Van Gemert | |
|---|---|---|---|---|
| 5,961,892 | A | 10/1999 | Gemert et al. | |
| 6,146,554 | A | 11/2000 | Melzig et al. | |
| 6,296,785 | B1* | 10/2001 | Nelson et al. | 252/586 |
| 6,469,076 | B1 | 10/2002 | Momoda et al. | |
| 6,723,859 | B2* | 4/2004 | Kawabata et al. | 549/332 |
| 2003/0096117 | A1 | 5/2003 | Kawabata et al. | |
| 2004/0014995 | A1* | 1/2004 | Kawabata et al. | 549/406 |

FOREIGN PATENT DOCUMENTS

| JP | 2002-161269 A | | 6/2002 |
|---|---|---|---|
| JP | 2002-161269 A | * | 6/2002 |
| JP | JP-2002-161269 A | | 6/2002 |
| JP | 02-524559 A | | 8/2002 |
| JP | 2002-524559 A | | 8/2002 |
| JP | 03-513017 A | | 4/2003 |
| JP | 2003-513017 A | | 4/2003 |
| WO | WO-96/14596 A1 | | 5/1996 |
| WO | WO-99/15518 A1 | | 4/1999 |
| WO | WO-00/35902 A1 | | 6/2000 |
| WO | WO-00/71544 A1 | | 11/2000 |
| WO | WO-01/19813 A1 | | 3/2001 |
| WO | WO-01/60811 A1 | | 8/2001 |
| WO | WO-03/011967 A1 | | 2/2003 |

* cited by examiner

*Primary Examiner*—Lorna M Douyon
*Assistant Examiner*—Bijan Ahvazi
(74) *Attorney, Agent, or Firm*—Birch, Stewart, Kolasch & Birch, LLP

(57) ABSTRACT

A chromene compound of this invention, as shown in the following formula:

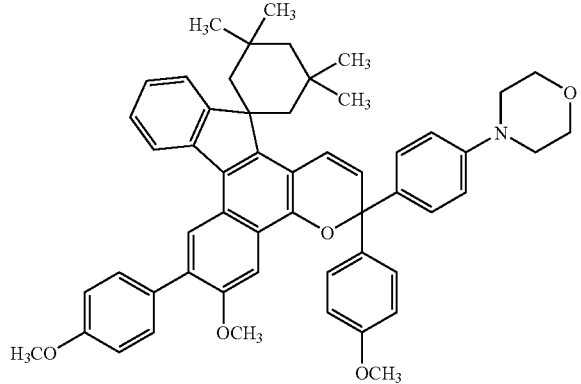

characterized by having an indeno(2,1-f)naphtho(1,2-b)pyran structure as a basic structure, and having a substituent which is a substituted or unsubstituted aryl group such as methoxyphenyl group, or a substituted or unsubsterituted heteroaryl group such as thienyl group bonding to a carbon atom at the seventh position of the indeno(2,1-f)naphtho(1, 2-b)pyran structure. The photochromic compound exhibits a color tone of a neutral tint when it develops a color, features a high color-developing sensitivity and a high fading rate, and has a good photochromic resistance.

5 Claims, 1 Drawing Sheet

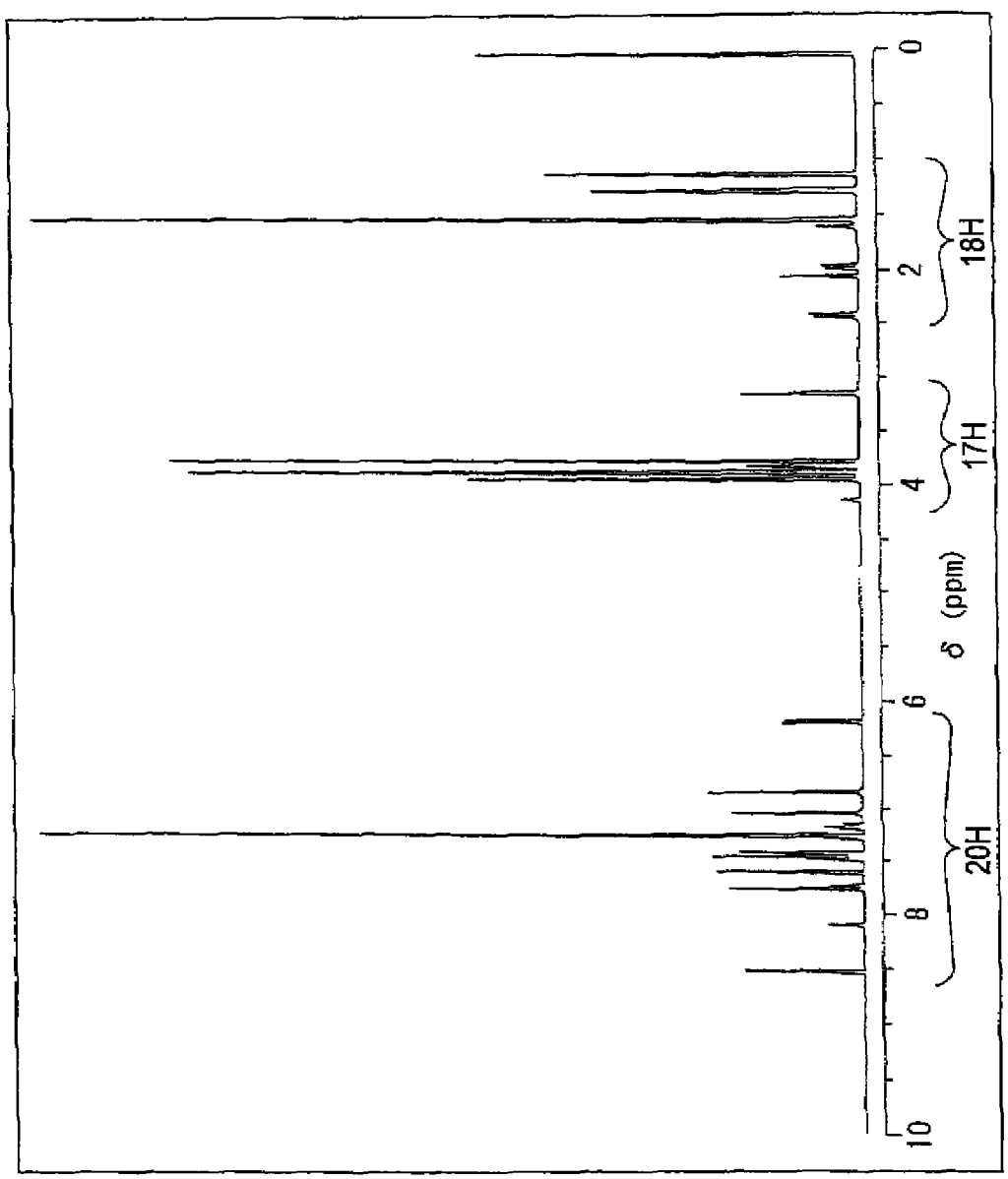

CHROMENE COMPOUND

TECHNICAL FIELD

The present invention relates to novel chromene compounds useful as photochromic compounds for photochromic spectacle lenses.

BACKGROUND ART

Photochromism is a reversible action of a compound which quickly changes the color when it is irradiated with light containing ultraviolet rays, such as the sunlight or the light of a mercury lamp, and resumes its initial color when it is no longer irradiated with light and is placed in a dark place. The compounds which have the above properties are called photochromic compounds and used for material of photochromic plastic lenses.

The photochromic compound used for the above application is required to be satisfying such properties that:
(1) The compound has a low coloring degree (low initial color) in a region of visible light of before being irradiated with ultraviolet rays;
(2) The compound exhibits a high coloring degree (hereinafter called color density) when it is irradiated with ultraviolet rays;
(3) The compound enables the color density to increase to a saturation at a high rate (has a high color-developing sensitivity) after it is irradiated with ultraviolet rays;
(4) The compound returns to the initial state at a high rate (has a high fading rate) after it is no longer irradiated with ultraviolet rays;
(5) Repetition of the reversible action of the compound is highly resistant; and
(6) The compound that is cured dissolves highly densely in a monomer composition that becomes a host material so as to be highly dispersed in the host material that is used.

As a photochromic compound capable of satisfying the above requirements, there has been known a chromene compound having an indeno(2,1-f)naphtho(1,2-b)pyran structure as a basic skeleton (see a pamphlet of International Laid-Open No. 99/15518 and a pamphlet of International Laid-Open No. 2001/60811).

On the other hand, it has been desired that the photochromic plastic lenses develop a color of a neutral tint such as grey or brown. The neutral tint is obtained by mixing a plurality of kinds of photochromic compounds that develop different color tones or, concretely, by mixing a compound of yellow to red color that has a maximum absorption when developing color of 430 to 530 nm and a compound of violet to blue color having a maximum absorption when developing color of 550 to 650 nm.

When the color is adjusted by the above method, however, there occur a variety of problems due to different photochromic properties of the compounds that are mixed together. For example, when a compound that develops yellow color has a recurring resistance that is smaller than that of a compound that develops blue color, there occurs a problem in that the color tone that is developed gradually changes into a bluish color tone after used for extended periods of time. Further, when a yellow compound has a color-developing sensitivity and a fading rate lower than those of a blue compound, there occurs a problem in that the color tone becomes bluish when the color is developing and the color tone becomes yellowish when the color is fading.

It is considered that the above problems can be solved by the use of a single compound that exhibits two or more absorption maxima when developing a color to develop a color of a neutral tint. As the photochromic compounds that exhibit two or more absorption maxima when developing a color, there have been known the compounds represented by the following formulas (A) to (C). However, there has not yet been known any photochromic compound that develops a color of a neutral tint while satisfying the requirements mentioned in (1) to (6) above.

That is, the chromene compound represented by the following formula (A) (see a pamphlet of International Laid-Open No. 96/14596):

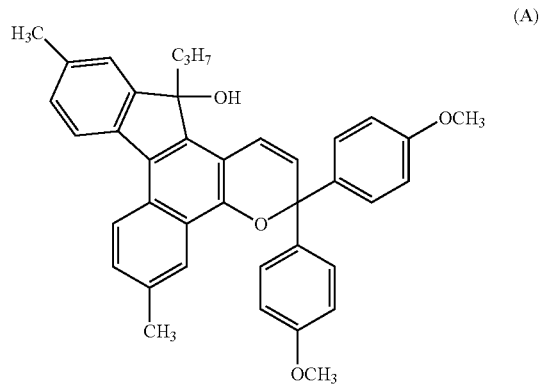

(A)

has an absorption over 430 to 530 nm, which is weaker than an absorption over 550 to 650 nm, and fails to develop a color tone of a neutral tint.

A chromene compound represented by the following formula (B) (see a pamphlet of International Laid-Open No. 2000/35902):

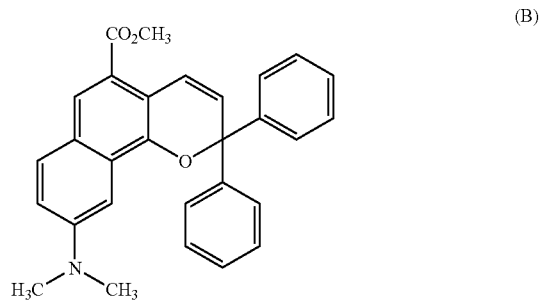

(B)

has a high initial color and a low recurring resistance.

The chromene compound represented by the following formula (C) (see a pamphlet of International Laid-Open No. 2001/19813):

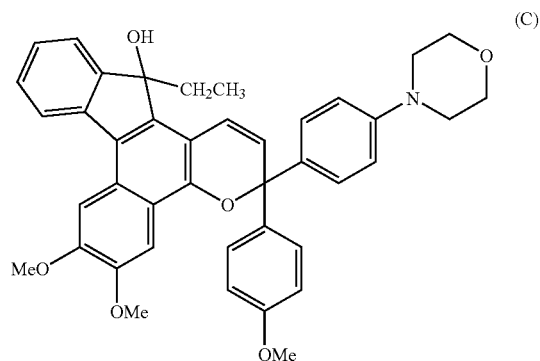

(C)

develops a color of a neutral tint but fades at a low rate and, besides, the recurring resistance is not high enough.

DISCLOSURE OF THE INVENTION

It is, therefore, an object of the present invention to provide a chromene compound exhibiting photochromic properties maintaining excellent resistance, i.e., developing a color tone of a neutral tint, exhibiting further improved photochromic properties as compared to the above-mentioned compounds, having a weak initial color, having a high color-developing sensitivity, exhibiting a high fading rate, getting colored little when aged, and permitting the color density to decrease little even after repetitively used, i.e., to provide a chromene compound capable of being highly densely dissolved in a monomer composition that becomes the base member to be used.

The present inventors have conducted a keen study in order to solve the above problems. As a result, the inventors have discovered that a chromene compound which has been known to exhibit excellent photochromic properties and which has an indeno(2,1-f)naphtho(1,2-b)pyran structure as a basic skeleton, develops a color of a neutral tint without impairing its excellent photochromic properties when a particular substituent is introduced into the seventh position of the indeno (2,1-f)naphtho(1,2-b)pyran structure, and have finished the present invention.

That is, according to the present invention, there is provided a chromene compound having an indeno(2,1-f)naphtho (1,2-b)pyran structure represented by the following formula:

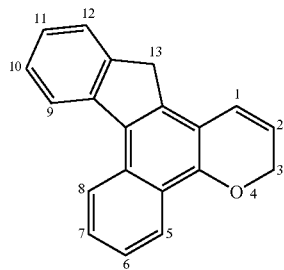

as a basic skeleton, wherein a substituted or unsubstituted aryl group or a substituted or unsubstituted heteroaryl group is bonded, as a substituent, to a carbon atom at the seventh position of the pyran structure.

According to the present invention, further, there is provided a photochromic composition containing the above chromene compound.

According to the present invention, further, there is provided a photochromic optical article having, as a constituent member, a high molecular molded body in which the above chromene compound is dispersed.

According to the present invention, there is further provided an optical article having, as a constituent member, an optical base member of which at least one surface is wholly or partly coated with a high molecular film, the high molecular film containing the chromene compound dispersed therein.

The chromene compound of the present invention not only exhibits excellent photochromic properties such as a color tone of a neutral tint when developing a color, a weak initial color, a high color-developing sensitivity, a high color density and a high fading rate even when it is dispersed in a solution or in a high molecular solid matrix but also exhibits excellent light resistance. Therefore, a photochromic lens that is produced by using the chromene compound of the invention quickly develops a dense neutral tint, quickly fades to resume the initial color tone when returned back to the indoors from the outdoors, and can be used for extended periods of time maintaining a high light resistance.

BRIEF DESCRIPTION OF THE DRAWING

FIG. 1 is a diagram of proton nucleus magnetic resonance spectra of a chromene compound of Example 1.

BEST MODE FOR CARRYING OUT THE INVENTION (Chromene Compounds)

The chromene compound of the present invention has an indeno(2,1-f)naphtho(1,2-b)pyran structure represented by the above-mentioned formula, i.e.,

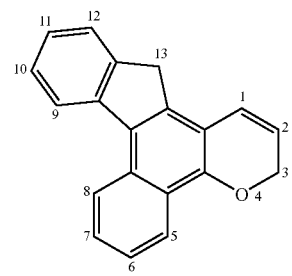

as a basic skeleton, and has a substituted or unsubstituted aryl group, or a substituted unsubstituted heteroaryl group, as a substituent {which corresponds to a group $R^5$ in the formula (1) that will appear later}, bonded to a carbon atom at the seventh position of the indeno(2,1-f)naphtho(1,2-b)pyran structure. It has been known that the chromene compound having the indeno(2,1-f)naphtho(1,2-b)pyran structure as a basic skeleton exhibits excellent photochromic properties. According to the present invention, the above particular substituent is introduced to the seventh position of the pyran structure making it possible to develop a dense neutral tint despite of a single compound yet maintaining its excellent photochromic properties.

In the following description, the indeno(2,1-f)naphtho(1, 2-b)pyran structure represented by the above formula is simply called "pyran structure".

<Substituted or Unsubstituted Aryl Groups>

There is no particular limitation on the substituted or unsubstituted aryl group to be bonded to the carbon atom at the seventh position of the pyran structure. However, color develops less if the group becomes too bulky. Desirably, therefore, the unsubstituted aryl group has 6 to 10 carbon atoms, and the substituted aryl group is the one in which 1 to 7 hydrogen atoms and, particularly, 1 to 4 hydrogen atoms of the unsubstituted aryl group have been substituted.

As the substituent in the above substituted aryl group, further, there can be exemplified at least the one selected from the group consisting of (s1) an unsubstituted alkyl group, (s2) an unsubstituted alkoxy group, (s3) an unsubstituted aralkoxy group, (s4) a substituted amino group, (s5) an unsubstituted aryl group, (s6) a substituted or unsubstituted heterocyclic group having a nitrogen atom as a hetero atom and bonded to the unsubstituted aryl group via the nitrogen atom, (s7) a condensed heterocyclic group in which the heterocyclic group (s6) is condensed with an aromatic hydrocarbon ring or an aromatic heterocyclic ring, (s8) a halogen atom, (s9) a cyano group, (s10) a nitro group, (s11) a hydroxy group and (s12) a trifluoromethyl group.

Though there is no particular limitation, it is desired that the unsubstituted alkyl group (s1) is an alkyl group having 1 to 4 carbon atoms. Preferred examples of the alkyl group include a methyl group, an ethyl group, an n-propyl group, an isopropyl group, an n-butyl group, a sec-butyl group and a t-butyl group.

Though there is no particular limitation, it is desired that the unsubstituted alkoxy group (s2) is an alkoxy group having 1 to 5 carbon atoms. Preferred examples of the alkoxy group include a methoxy group, an ethoxy group, an n-propoxy group, an isopropoxy group, an n-butoxy group, a sec-butoxy group and a t-butoxy group.

Though there is no particular limitation, it is desired that the unsubstituted aralkoxy group (s3) is an aralkoxy group having 6 to 10 carbon atoms. Preferred examples of the aralkoxy group include a phenoxy group and a naphthoxy group.

Though there is no particular limitation, it is desired that the substituted amino group (s4) is a monoalkylamino group substituted with an unsubstituted alkyl group or with an unsubstituted aryl group, or is a dialkylamino group, a monoarylamino group or a diarylamino group. Concrete examples of the preferred substituted amino group include a methylamino group, an ethylamino group, a phenylamino group, a dimethylamino group, a diethylamino group and a diphenylamino group.

Though there is no particular limitation, it is desired that the unsubstituted aryl group (s5) is an aryl group having 6 to 10 carbon atoms. Preferred examples of the aryl group include phenyl group and naphthyl group.

Concrete examples of the preferred substituted or unsubstituted heterocyclic ring (s6) or condensed heterocyclic group (s7) include a morpholino group, a piperidino group, a pyrrolidinyl group, a piperazino group, an N-methylpiperazino group and an indolinyl group.

As the halogen atom (s8), there can be exemplified a fluorine atom, a chlorine atom, a bromine atom and an iodine atom.

In the present invention, a phenyl group or a naphthyl group is particularly desired as the unsubstituted aryl group bonded to a carbon atom at the seventh position of the pyran structure. As the substituted aryl group, further, there can be particularly preferably used a methylphenyl group, an ethylphenyl group, a methoxyphenyl group, an ethoxyphenyl group, a dimethoxyphenyl group, a trimethoxyphenyl group, a morpholinophenyl group, a methoxybiphenyl group and a dimethylaminophenyl group.

<Substituted or Unsubstituted Heteroaryl Groups>

There is no particular limitation on the substituted or unsubstituted heteroaryl group to be bonded to the carbon atom at the seventh position of the pyran structure. However, color develops less if the group becomes too bulky like in the case of the above aryl group. Desirably, therefore, the unsubstituted heteroaryl group has 4 to 12 carbon atoms. Further, the substituted heteroaryl group is the one in which 1 to 9 hydrogen atoms and, particularly, 1 to 4 hydrogen atoms of the unsubstituted heteroaryl group have been substituted.

As the substituent in the substituted heteroaryl group, there can be exemplified at least the one selected from the group consisting of an unsubstituted alkyl group, an unsubstituted alkoxy group, an unsubstituted aralkoxy group, an substituted amino group, an unsubstituted aryl group, a substituted or unsubstituted heterocyclic group having a nitrogen atom as a hetero atom and bonded to the heteroaryl group via the nitrogen atom, a condensed heterocyclic group in which the heterocyclic group is condensed with an aromatic hydrocarbon ring or an aromatic heterocyclic ring, a halogen atom, a cyano group, a nitro group, a hydroxy group and a trifluoromethyl group. Concrete examples of the substituent in the substituted heteroaryl group may include those substituents same as those for the above-mentioned substituted aryl groups.

As the unsubstituted heteroaryl group bonded to the seventh position of the pyran structure in the present invention, there can be particularly desirably used a thienyl group, a furyl group, a pyrrolinyl group, a pyridyl group, a benzothienyl group, a benzofuranyl group and a benzopyrrolinyl group. As the substituted heteroaryl group, there can be particularly preferably used methylthienyl group, methoxythienyl group, dimethylthienyl group, dimethoxythienyl group, dimethylaminothienyl group, biphenylaminothienyl group, methylfuryl group, methoxyfuryl group, dimethylfuryl group, dimethoxyfuryl group, dimethylaminofuryl group, biphenylaminofuryl group, methylpyrrolinyl group, methoxypyrrolinyl group, dimethylpyrrolinyl group, dimethoxypyrrolinyl group, dimethylaminopyrrolinyl group, biphenylaminopyrrolinyl group, methylpyridyl group, methoxypyridyl group, dimethylpyridyl group, dimethoxypyridyl group, dimethylaminopyridyl group, biphenylaminopyridyl group, methylbenzothienyl group, methoxybenzothienyl group, dimethylbenzothienyl group, dimethoxybenzothienyl group, dimethylaminobenzofuranyl group and biphenylaminobenzopyrrolinyl group.

Among the chromene compounds of the present invention having a particular substituent at the seventh position of the pyran structure, it is desired to use a chromene compound represented by the following formula (1) from the standpoint obtaining a color tone of a neutral tint when a color is developed, a high color-developing sensitivity, a fast fading rate and good photochromic resistance:

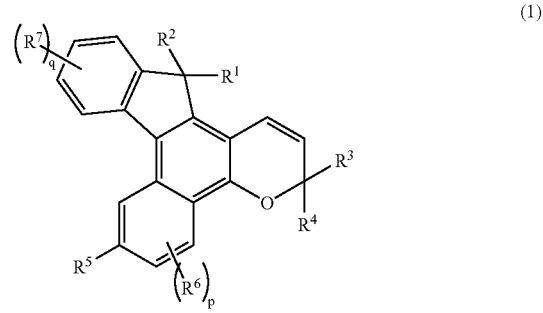

(1)

wherein $R^5$ is a substituted or unsubstituted aryl group, or a substituted or unsubstituted heteroaryl group bonded to the seventh position of the pyran structure, p representing the number of the groups $R^6$ is an integer of 0 to 3, and q representing the number of $R^7$ is an integer of 0 to 4.

<$R^1$ and $R^2$>

In the formula (1), $R^1$ and $R^2$ are groups independent from each other and are, respectively, groups (i-1) to (i-8) described below, or are groups which are bonded together and are spiro-bonded to the thirteenth position of the pyran structure to form rings of (ii-1) to (ii-4) described below.

Examples of Groups of when $R^1$ and $R^2$ are Existing as Independent Groups:

(i-1) hydrogen atoms;
(i-2) hydroxy groups;
(i-3) substituted or unsubstituted alkyl groups such as methyl groups, ethyl groups, n-propyl groups, isopropyl groups, n-butyl groups, sec-butyl groups or t-butyl groups;

(i-4) substituted or unsubstituted cycloalkyl groups such as cyclobutyl groups, cyclopentyl groups, cyclohexyl groups, cycloheptyl groups or cyclooctyl groups;

(i-5) substituted or unsubstituted aryl groups such as phenyl groups, naphthyl groups, methoxyphenyl groups or dimethoxyphenyl groups;

(i-6) halogen atoms such as fluorine atoms, chlorine atoms, bromine atoms or iodine atoms;

(i-7) groups represented by the formula, —C(O)W, wherein W is a hydroxy group, an unsubstituted alkyl group having 1 to 6 carbon atoms, an unsubstituted alkoxy group having 1 to 6 carbon atoms, an unsubstituted phenyl group, a mono-substituted phenyl group, an unsubstituted amino group, a monoalkylamino group having, as a substituent, one unsubstituted alkyl group having 1 to 6 carbon atoms, or a dialkylamino group having, as substituents, two unsubstituted alkyl groups having 1 to 6 carbon atoms, and, preferably, carboxyl groups, acetyl groups or ethylcarbonyl groups;

(i-8) groups represented by the formula, —OR$^8$, wherein R$^8$ is an unsubstituted alkyl group having 1 to 6 carbon atoms, a mono-substituted alkyl group having one unsubstituted phenyl group as a substituent and having 1 to 3 carbon atoms (without including carbon atoms of the substituent), a mono-substituted alkyl group having, as a substituent, a mono-substituted phenyl group with one unsubstituted alkyl group of 1 to 6 carbon atoms, and having 1 to 3 carbon atoms (without including carbon atoms of the substituent), a mono-substituted alkyl group having, as a substituent, a mono-substituted phenyl group with one unsubstituted alkoxy group of 1 to 6 carbon atoms, and having 1 to 3 carbon atoms (without including carbon atoms of the substituent), a mono-substituted alkyl group having, as a substituent, one alkoxy group with 1 to 6 carbon atoms, and having 2 to 4 carbon atoms (without including carbon atoms of the substituent), an unsubstituted cycloalkyl group having 3 to 7 carbon atoms, a mono-substituted cycloalkyl group having, as a substituent, one alkyl group of 1 to 4 carbon atoms, and having 3 to 7 carbon atoms that constitute a ring, a chloroalkyl group having 1 to 6 carbon atoms, a fluoroalkyl group having 1 to 6 carbon atoms, an unsubstituted allyl group, a group represented by the formula —CH(R$^9$)X (wherein R$^9$ is a hydrogen atom or an unsubstituted alkyl group with 1 to 3 carbon atoms, X is —CN, —CF$_3$ or —COOR$^{10}$, R$^{10}$ being a hydrogen atom or an unsubstituted alkyl group with 1 to 3 carbon atoms), or a group represented by the formula —C(O)Y (wherein Y is a hydrogen atom, an unsubstituted alkyl group having 1 to 6 carbon atoms, an unsubstituted alkoxy group having 1 to 6 carbon atoms, an unsubstituted aryl group, a mono- or di-substituted aryl group, an unsubstituted phenoxy group, a mono- or di-substituted phenoxy group having one or two unsubstituted alkyl groups of 1 to 6 carbon atoms as substituents, a mono- or di-substituted phenoxy group having one or two unsubstituted alkoxy groups of 1 to 6 carbon atoms as substituents, an unsubstituted amino group, a mono- or di-substituted amino group having one or two unsubstituted alkyl groups of 1 to 6 carbon atoms as substituents, a mono-substituted amino group having an unsubstituted phenyl group as a substituent, a mono-substituted amino group having, as a substituent, a mono- or di-substituted phenyl group to which are bonded one or two unsubstituted alkyl groups of 1 to 6 carbon atoms, or a mono-substituted amino group having, as a substituent, a mono- or di-substituted phenyl group to which are bonded one or two unsubstituted alkoxy groups of 1 to 6 carbon atoms), and, preferably, methyl ether groups, ethyl ether groups, propyl ether groups, phenylmethyl ether groups or those having a group R$^8$ represented by the formula —C(O)Y (such as aldehyde groups, carboxyl groups or phenylcarbonyl groups).

Examples of Rings in which R$^1$ and R$^2$ are Bonded Together and are Independently Spiro-Bonded to the Thirteenth Position of the Pyran Structure:

(ii-1) a substituted or unsubstituted aliphatic ring having 3 to 20 carbon atoms that constitute the ring, such as a cyclopentane ring, a cyclohexane ring, a cyclooctane ring, a cycloheptane ring, a norbornane ring, a bicyclononane ring or an adamantane ring;

(ii-2) a condensed polycyclic ring in which a substituted or unsubstituted aromatic ring or a substituted or unsubstituted aromatic heterocyclic ring is condensed with the above aliphatic ring (ii-1);

(ii-3) a substituted or unsubstituted heterocyclic ring having 3 to 20 carbon atoms that constitute the ring, such as a thiophene ring, a furan ring or a pyridine ring;

(ii-4) a condensed polycyclic ring in which a substituted or unsubstituted aromatic ring or a substituted or unsubstituted aromatic heterocyclic ring is condensed with the above heterocyclic ring (ii-3).

In the present invention, it is desired that the group R$^1$ and the group R$^2$ in the formula (1) are bonded together to form a ring, and are, particularly, forming the aliphatic ring (ii-1) or the condensed polycyclic ring (ii-2) from the standpoint of quickening the fading rate, and are, further, forming the aliphatic ring (ii-1) from the standpoint of decreasing the initial color. Preferred examples of the aliphatic ring (ii-1) formed by R$^1$ and R$^2$ are monocyclic rings such as cyclohexane ring, cyclooctane ring and cycloheptane ring; bicyclic rings such as norbornane ring and bicyclononane ring; and tricyclic rings such as adamantane ring, which may have at least one lower alkyl group having not more than 4 carbon atoms, such as methyl group as a substituent. Further, preferred examples of the condensed polycyclic ring (ii-2) formed by R$^1$ and R$^2$ may be the preferred aliphatic rings (ii-1) exemplified above condensed with at least an aromatic ring (e.g., benzene ring, naphthalene ring or anthracene ring). Here, any carbon atom of the above ring may be the one at the thirteenth position of the pyran structure.

In the present invention, the most preferred representative rings formed by being bonded with R$^1$ and R$^2$ are expressed by the following formulas. In the following formulas, a carbon atom at a position designated at 13 is the carbon atom at the thirteenth position of the pyran structure.

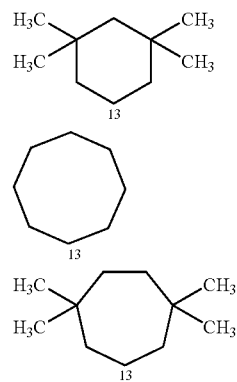

-continued

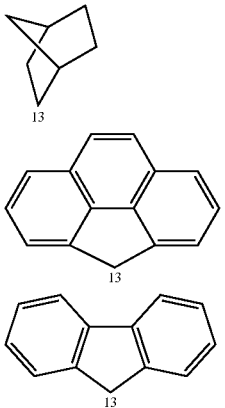

<R³ and R⁴>

In the above formula (1), the groups R³ and R⁴ may be independent from each other or may be bonded together to form a ring. Examples of the independent groups include substituted or unsubstituted aryl groups, substituted or unsubstituted heteroaryl groups, unsubstituted alkyl groups, or aliphatic groups having a double bond or a triple bond between the carbon atoms. Examples of the rings formed by being bonded with R³ and R⁴ include an aliphatic hydrocarbon ring and an aromatic hydrocarbon ring.

As the substituted or unsubstituted aryl group or as the substituted or unsubstituted heteroaryl groups, there can be exemplified those groups same as the groups described above already as groups to be bonded to the carbon atom at the seventh position of the pyran structure (the same also holds for the group R⁵ that will be described later). The unsubstituted alkyl group is the same as the unsubstituted alkyl group (i-3) described above concerning the group R¹.

As the aliphatic group having a double bond or a triple bond between the carbon atoms, there can be exemplified the groups represented by the following formula (2) or (3).

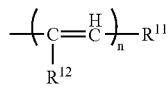 (2)

 (3)

In the above formula (2) or (3), $R^{11}$ is a substituted or unsubstituted aryl group or a substituted or unsubstituted heteroaryl group, n is an integer of 1 to 3, $R^{13}$ is a substituted or unsubstituted aryl group or a substituted or unsubstituted heteroaryl group, and m is an integer of 1 to 3.

In the above formula (2), the substituted or unsubstituted aryl group and the substituted or unsubstituted heteroaryl group represented by $R^{11}$, too, are the same groups as those bonded to the carbon atom at the seventh position of the pyran structure described above, and $R^{12}$ is a hydrogen atom, an unsubstituted alkyl group or a halogen atom (e.g., fluorine atom, chlorine atom, bromine atom or iodine atom). As the unsubstituted alkyl group, there can be exemplified lower alkyl groups having not more than 4 carbon atoms, such as methyl group, ethyl group and propyl group. Further, n is an integer of 1 to 3 but is desirably 1 from the standpoint of easy availability of the starting materials.

Preferred examples of the aliphatic group having a double bond between the carbon atoms represented by the formula (2) include phenyl-ethenyl group, (4-(N,N-dimethylamino)phenyl)-ethenyl group, (4-(N,N-diethylamino)phenyl)-ethenyl group, (4-morpholinophenyl)-ethenyl group, (4-piperidinophenyl)-ethenyl group, (4-julolidinophenyl)-ethenyl group, (4-methoxyphenyl)-ethenyl group, (4-methylphenyl)-ethenyl group, (2-(N,N-dimethylamino)phenyl)-ethenyl group, (2-methoxyphenyl)-ethenyl group, phenyl-1-methylethenyl group, (4-(N,N-dimethylamino)phenyl)-1-methylethenyl group, (4-methoxyphenyl)-1-methylethenyl group, phenyl-1-fluoroethenyl group, (4-(N,N-dimethylamino)phenyl)-1-fluoroethenyl group, 2-thienyl-ethenyl group, 2-furyl-ethenyl group, 2-(N-methyl)pyrrolinyl-ethenyl group, 2-benzothienyl-ethenyl group, 2-benzofuranyl-ethenyl group and 2-(N-methyl)indolyl-ethenyl group.

In the above formula (3), the substituted or unsubstituted aryl group and the substituted or unsubstituted heteroaryl group represented by $R^{13}$, too, are the same groups as those bonded to the carbon atom at the seventh position of the pyran structure like those of $R^{11}$ above. Further, m is an integer of 1 to 3 but is desirably 1 from the standpoint of easy availability of the starting materials.

Preferred examples of the aliphatic group having a triple bond between the carbon atoms represented by the formula (3) include phenyl-ethynyl group, (4-(N,N-dimethylamino)phenyl)-ethynyl group, (4-(N,N-diethylamino)phenyl)-ethynyl group, (4-morpholinophenyl)-ethynyl group, (4-piperidinophenyl)-ethynyl group, (4-julolidinophenyl)-ethynyl group, (4-methoxyphenyl)-ethynyl group, (4-methylphenyl)-ethynyl group, (2-(N,N-dimethylaminophenyl)-ethynyl group, (2-methoxyphenyl)-ethynyl group, 2-thienyl-ethynyl group, 2-furyl-ethynyl group, 2-(N-methyl)pyrrolinyl-ethynyl group, 2-benzothienyl-ethynyl group, 2-benzofuranyl-ethynyl group and 2-(N-methyl)indolyl-ethynyl group.

As the ring formed by being bonded by R³ and R⁴, there can be exemplified an aliphatic hydrocarbon ring and an aromatic hydrocarbon ring as described earlier. As the aliphatic hydrocarbon ring, there can be preferably exemplified an adamantane ring, a bicyclononane ring and a norbornane ring though there is no particular limitation. As the aromatic hydrocarbon ring, further, there can be exemplified a fluorene ring though there is no particular limitation.

In the present invention, it is desired that at least either R³ or R⁴ is a substituted or unsubstituted aryl group, or a substituted or unsubstituted heteroaryl group, or a group having these groups as substituents. Most desirably, at least either R³ or R⁴ is any one of the groups described in (a) to (j) below.

(a) A substituted aryl group or a substituted heteroaryl group having a substituted amino group as a substituent;
(b) A substituted aryl group or a substituted heteroaryl group having, as a substituent, a substituted or unsubstituted heterocyclic group that has a nitrogen atom as a hetero atom and is bonded to the aryl group or to the heteroaryl group via the nitrogen atom;
(c) A substituted aryl group or a substituted heteroaryl group having an unsubstituted alkoxy group as a substituent;
(d) A substituted aryl group or a substituted heteroaryl group having, as a substituent, a condensed heterocyclic group in which the heterocyclic group in (b) above is condensed with an aromatic hydrocarbon ring or an aromatic heterocyclic ring;
(e) A group represented by the formula (2) in which $R^{11}$ is a substituted aryl group or a substituted heteroaryl group having a substituted amino group as a substituent;
(f) A group represented by the formula (2) in which $R^{11}$ is a substituted aryl group or a substituted heteroaryl group having, as a substituent, a substituted or unsubstituted heterocyclic group having a nitrogen atom as a hetero atom and is bonded to the aryl group or to the heteroaryl group via the nitrogen atom;

(g) A group represented by the formula (2) in which $R^{11}$ is a substituted aryl group or a substituted heteroaryl group having, as a substituent, a condensed heterocyclic group in which the heterocyclic group in (e) above is condensed with an aromatic hydrocarbon ring or an aromatic heterocyclic ring;

(h) A group represented by the formula (3) in which $R^{13}$ is a substituted aryl group or a substituted heteroaryl group having a substituted amino group as a substituent;

(i) A group represented by the formula (3) in which $R^{13}$ is a substituted aryl group or a substituted heteroaryl group having, as a substituent, a substituted or unsubstituted heterocyclic group that has a nitrogen atom as a hetero atom and is bonded to the aryl group or the heteroaryl group via the nitrogen atom; or (j) A group represented by the formula (3) in which $R^{13}$ is a substituted aryl group or a substituted heteroaryl group having, as a substituent, a condensed heterocyclic group in which the heterocyclic group in (h) above is condensed with an aromatic hydrocarbon ring or an aromatic heterocyclic ring.

In the substituted aryl groups described in (a) to (d) above, there is no particular limitation on the positions of the substituents or on the total number thereof. When the aryl group is a phenyl group, however, it is desired that the substituent is located at the third position or the fourth position, and its number is 1. From the standpoint of improving the resistance of photochromic properties, further, it is particularly desired that the substituent is located at the fourth position. Preferred examples of the substituted aryl group include 4-(N,N-dimethylamino)phenyl group, 4-(N,N-diethylamino)phenyl group, 4-(N,N-diphenylamino)phenyl group, 4-morpholinophenyl group, 4-piperidinophenyl group, 3-(N,N-dimethylamino)phenyl group, 4-(2,6-dimethylpiperidino)phenyl group and 4-methoxyphenyl group.

In the substituted heteroaryl groups described in (a) to (d) above, there is no particular limitation on the positions of the substituents or on the total number thereof. It is, however, desired that number thereof is 1. Preferred examples of the substituted heteroaryl group include 4-(N,N-dimethylamino)thienyl group, 4-(N,N-diethylamino)furyl group, 4-(N,N-diphenylamino)thienyl group, 4-morpholinopyrrolinyl group, 6-piperidinobenzothienyl group, and 6-(N,N-dimethylamino)benzofuranyl group.

In the groups represented by the formula (2) in (e) to (g) above, $R^{11}$ in the formula (2) represents the same substituted aryl groups or the substituted heteroaryl groups as those of (a) to (d) above. In the groups represented by the formula (3) in (h) to (j) above, further, $R^{13}$ in the formula (3) represents the same substituted aryl groups or the substituted heteroaryl groups as those of (a) to (d) above.

<$R^5$>

In the above formula (1), $R^5$ is a substituted or unsubstituted aryl group or a substituted or unsubstituted heteroaryl group. It was described already that the group $R^5$ has been bonded to the carbon atom at the seventh position of the pyran structure.

<$R^6$ and $R^7$>

In the above formula (1), $R^6$ and $R^7$ are independent from each other, and are unsubstituted alkyl groups, unsubstituted alkoxy groups, unsubstituted aralkoxy groups, unsubstituted or substituted amino groups, cyano groups, substituted or unsubstituted aryl groups, halogen atoms, unsubstituted aralkyl groups, substituted or unsubstituted heterocyclic groups having a nitrogen atom as a hetero atom and in which the nitrogen atom is bonded to a benzo ring, or condensed heterocyclic groups in which the heterocyclic group is condensed with an aromatic hydrocarbon ring or an aromatic heterocyclic ring.

Among various groups represented by $R^6$ and $R^7$, the unsubstituted aralkyl group has no particular limitation and preferably has 7 to 11 carbon atoms as exemplified by benzyl group, phenylethyl group, phenylpropyl group and phenylbutyl group. The substituted or unsubstituted aryl group is the same as the one exemplified concerning the groups bonded to the seventh position of the pyran structure, and is the same as the substituted or unsubstituted aryl group $R^5$. Other substituents are the same as the groups (s1), (s2), (s3), (s4), (s5), (s6), (s7) and (s8) exemplified as the substituents possessed by the substituted aryl groups.

The number (p) of the groups $R^6$ is 0 to 3, and is desirably not larger than 2. When there are a plurality of groups $R^6$ (p is not smaller than 2), the groups $R^6$ present in a plural number may be different from each other. There is no particular limitation on the positions to where $R^6$ are bonded, and sixth and/or eighth positions are desired.

When bonded to the sixth position or the eighth position in the present invention, it is desired that the group $R^6$ is the one having an intermediate degree of electron-donating property with a Hammett number in a range of −0.49 to −0.20 or having a weak electron-donating property with a Hammett number in a range of −0.19 to −0.01 among other substituents from the standpoint of intensifying double-peaking property while suppressing the initial color. The Hammett number (σ) is determined based on the Hammett rule in which determines the electronic effect of a substituent bonded to a π electron system is quantified from basis for a dissociation constant Ka of m- and p-substituted benzoic acids.

Concrete examples of the group having an intermediate degree of electron-donating property with a Hammett number of −0.49 to −0.2 include alkoxy groups, such as methoxy group (σ=−0.28), ethoxy group (σ=−0.21) and propoxy group (σ=−0.26); and p-alkylaminophenyl groups such as p-dimethylaminophenyl group (σ=−0.22) and p-diethylaminophenyl group (σ=−0.22).

As the group having a weak electron-donating property with a Hammett number of −0.19 go −0.01, there can be exemplified alkoxyphenyl groups such as p-methoxyphenyl group (σ=−0.04) and o, p-dimethoxyphenyl group (σ=−0.08); aryl groups such as phenyl group (σ=−0.01), 1-naphthyl group (σ=−0.08) and 2-naphthyl group (σ=−0.02); p-nitrogen atom-containing heterocyclic aryl groups such as p-morpholinophenyl group (σ=−0.16); heteroaryl groups such as thienyl group (σ=−0.1); alkyl groups such as methyl group (σ=−0.14), ethyl group (σ=−0.13) and propyl group (σ=−0.12); and cycloalkyl groups such as cyclohexyl group (σ=−0.16).

The number (q) of the groups $R^7$ is an integer of 0 to 4, which, however, is desirably not larger than 2. When there are a plurality of groups $R^7$ (q is not smaller than 2), the groups $R^7$ present in a plural number may be different from each other. There is no particular limitation on the positions to where $R^7$ are bonded.

The chromene compound of the present invention is particularly desirably represented by the following formula (4) from the standpoint of obtaining good photochromic properties while easily developing a color of a neutral tint.

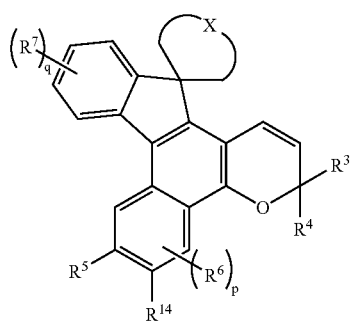

(4)

wherein $R^3$, $R^4$, $R^5$, $R^6$, $R^7$ and q are as defined in the above formula (1), $R^{14}$ is an electron-donating group having a Hammett number of −0.49 to −0.01 among the groups represented by $R^6$ in the above formula (1), and p is an integer of 0 to 2.

In the above formula (4), a group represented by the following formula (5),

(5)

is a divalent aliphatic hydrocarbon cyclic group which may have at least one substituent selected from substituted or unsubstituted alkyl group, substituted or unsubstituted alkoxy group or substituted or unsubstituted amino group, and corresponds to a divalent group comprising an aliphatic ring (ii-1) formed by being bonded by the groups $R^1$ and $R^2$ in the formula (1).

In the most preferred chromene compound of the present invention, $R^4$ in the above formula (4) is "a substituted aryl group or a substituted heteroaryl group having an unsubstituted amino group as a substituent", "a substituted aryl group or a substituted heteroaryl group having, as a substituent, a substituted or unsubstituted heterocyclic group that has a nitrogen atom as a hetero atom and is bonded to the aryl group or to the heteroaryl group via the nitrogen atom", "a substituted aryl group or a heteroaryl group having an unsubstituted alkoxy group as a substituent", or "the above substituted aryl group or the substituted heteroaryl group of which the heterocyclic group is condensed with an aromatic hydrocarbon ring or an aromatic heterocyclic ring to form a condensed heterocyclic group".

Described below are concrete examples of the chromene compound that are particularly preferred in the present invention.

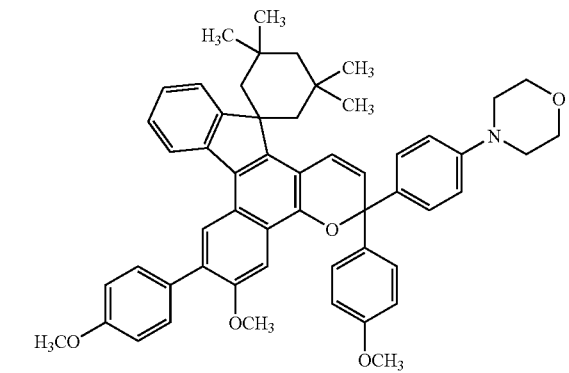

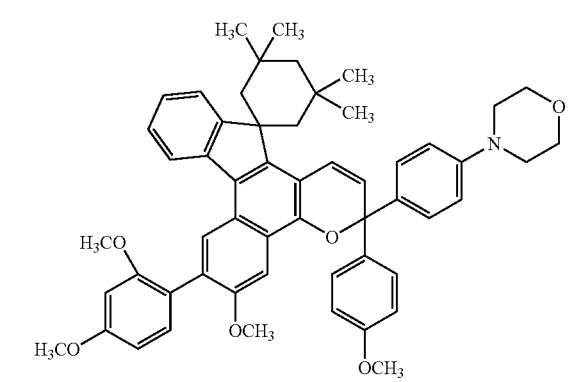

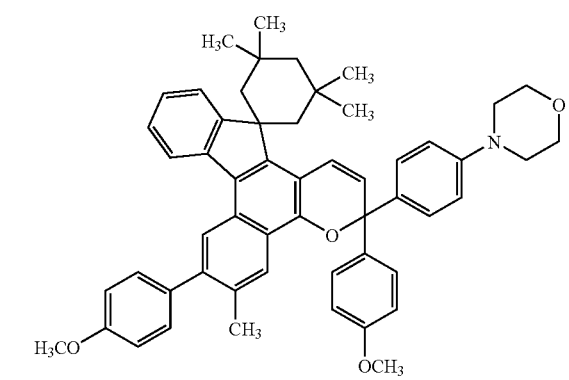

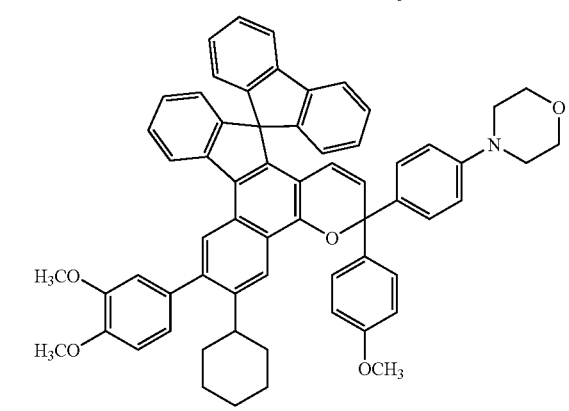

-continued

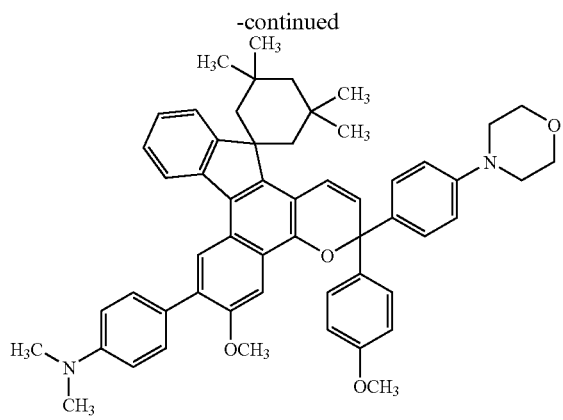

The chromene compounds of the present invention usually exist as solids or viscous liquids which are colorless, faintly yellow or faintly green under normal temperature and normal pressure, and can be confirmed by the following means (a) to (c).
(a) Upon measuring the proton nuclear magnetic resonance spectra ($^1$H-NMR), there appear peaks near δ: 5.0 to 9.0 ppm based on the aromatic proton and the proton of alkene. Further, the number of protons of the bonded groups can be known by comparing their spectral intensities.
(b) The compositions of the corresponding products can be determined by the elemental analysis.
(c) Upon measuring the $^{13}$C-nuclear magnetic resonance spectra ($^{13}$C-NMR), there appear peaks based on the carbon atom of an aromatic hydrocarbon group near δ: 110 to 160 ppm, peaks based on the carbon atoms of an alkene and an alkyne near δ: 80 to 140 ppm, and peaks based on the carbon atoms of an alkyl group and an alkylene group near δ: 20 to 80 ppm.

<Production of Chromene Compounds>

The chromene compounds of the present invention can be produced by any synthesizing method without limitation. For example, the chromene compound represented by the above formula (1) can be preferably produced by a method described below. In the following description, reference numerals in the formula has meanings as described above concerning the above formulas.

Namely, the chromene compound can be preferably produced by a method of reacting a hydroxy-fluorene derivative represented by the following formula (6),

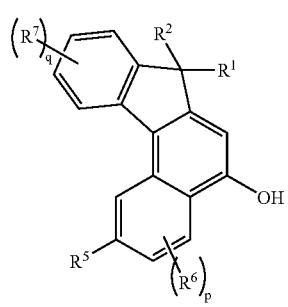
(6)

with a propargyl alcohol derivative represented by the following formula (7),

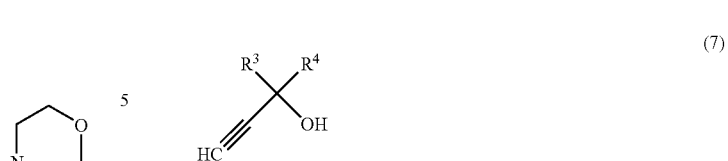

The reaction ratio of the hydroxy-fluorene derivative with the propargyl alcohol derivative can be selected over a wide range, but is usually selected in a range of 1;10 to 10:1 (molar ratio). As the acidic catalyst, there can be used sulfuric acid, benzenesulfonic acid, p-toluenesulfonic acid or acidic alumina in an amount in a range of 0.1 to 10 parts by weight per a total amount of 100 parts by weight of the hydroxy-fluorene derivative and the propargyl alcohol derivative. The preferable reaction temperature is usually 0 to 200° C., and the preferable solvent is a nonprotonic organic solvent, such as N-methylpyrrolidone, dimethylformamide, tetrahydrofuran, benzene or toluene. There is no particular limitation on the method of purifying the product obtained by the above reaction. For example, the product is refined through the silica gel column followed by recrystallization.

Though there is no particular limitation, the hydroxy-fluorene derivative represented by the above formula (6) can be synthesized by a method which is described below.

First, a carboxylic acid derivative represented by the following formula (8),

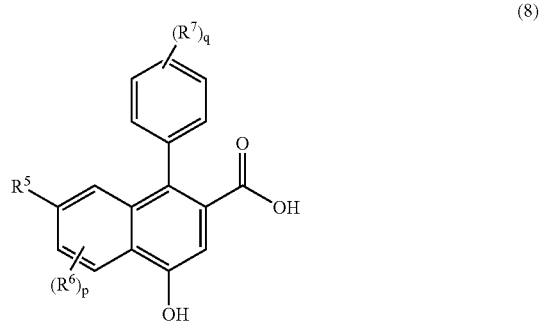
(8)

is changed to an amine by using the method such as the Curtius dislocation, Hofmann dislocation or Lossen dislocation, then a diazonium salt is prepared by using the amine. The diazonium salt is converted into a bromide by the Sandmeyer reaction, then the obtained bromide is reacted with magnesium or lithium to prepare an organometal reagent. The organic metal reagent is reacted with a ketone represented by the following formula (9),

at −10 to 70° C. for 10 minutes to 4 hours in an organic solvent to obtain an alcohol derivative represented by the following formula (10),

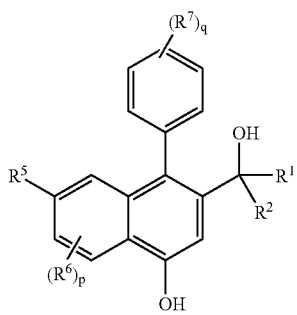

(10)

The alcohol derivative is reacted under a neutral to acidic condition at 10 to 120° C. for 10 minutes to 2 hours to turn the alcohol derivative into a spiro form thereof thereby to synthesize a desired hydroxy-fluorene derivative. In this reaction, the reaction ratio of the above organometal reagent and the ketone represented by the above formula (9) is selected from a wide range, but is usually selected from a range of 1:10 to 10:1 (molar ratio). The preferable reaction temperature is usually −10 to 70° C., and the preferable solvent is a non-protonic organic solvent such as diethyl ether, tetrahydrofurane, benzene or toluene. It is further desired that the alcohol derivative is turned into a spiro form thereof under the neutral to acidic condition by using an acidic catalyst such as acetic acid, hydrochloric acid, sulfuric acid, benzenesulfonic acid, p-toluenesulfonic acid, or acidic alumina. The acidic catalyst is desirably used in an amount in a range of 0.1 to 10 parts by weight per 100 parts by weight of the alcohol derivative. The alcohol derivative is turned into a spiro form thereof by using a solvent such as tetrahydrofurane, benzene or toluene.

Further, the propargyl alcohol derivative represented by the general formula (7) can be synthesized by a variety of methods and can, for example, be easily synthesized by reacting a ketone derivative corresponding to the above general formula (9) with a metal acetylene compound such as lithium acetylide.

The thus synthesized chromene compound of the present invention dissolves well in a general organic solvent such as toluene, chloroform or tetrahydrofurane. The solvent in which the chromene compound of the general formula (1) is dissolved is usually colorless and clear, and exhibits a good photochromism. That is, the chromene compound is quickly developing a color when it is irradiated with sunlight or ultraviolet rays and reversibly and quickly resuming its initial colorless state when the irradiation of light is interrupted.

Further, the chromene compound of the present invention exhibits similar photochromic properties even in a high molecular solid matrix. The high molecular solid matrix may be any one provided it permits the chromene compound of the present invention to be homogeneously dispersed therein. Optically preferably, there can be exemplified such thermoplastic resins as methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethyl methacrylate), polydimethylsiloxane, and polycarbonate.

A thermosetting resin obtained by polymerizing a radically polymerizable polyfunctional monomer can also be used as the high molecular matrix. As the radically polymerizable polyfunctional monomer, there can be exemplified polyvalent acrylic and polyvalent methacrylic ester compounds such as ethylene glycol diacrylate, diethylene glycol dimethacrylate, triethylene glycol dimethacrylate, tetraethylene glycol dimethacrylate, ethylene glycolbisglycidyl methacrylate, bisphenol A dimethacrylate, 2,2-bis(4-methacryloyloxyethoxyphenyl)propane, and 2,2-bis(3,5-dibromo-4-methacryloyloxyethoxyphenyl)propane; polyvalent allyl compounds such as diallyl phthalate, diallyl terephthalate, diallyl isophthalate, diallyl tartrate, diallyl epoxysuccinate, diallyl fumarate, diallyl chloroendoate, diallyl hexaphthalate, diallyl carbonate, allyl diglycol carbonate and trimethylolpropanetriallyl carbonate; polyvalent thioacrylic and polyvalent thiomethacrylic ester compounds such as 1,2-bis(methacryloylthio)ethane, bis(2-acryloylthioethyl)ether, and 1,4-bis(methacryloylthiomethyl)benzene; acrylic ester compounds and methacrylic ester compounds such as glycidyl acrylate, glycidyl methacrylate, β-methylglycidyl methacrylate, bisphenol A-monoglycidyl ether methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate, 3-glycidyloxy-2-hydroxypropyloxy)-2-hydroxypropyl acrylate; and divinylbenzene.

Further, a copolymer obtained by copolymerizing the above radically polymerizable polyfunctional monomer with a radically polymerizable monofunctional monomer, too, can be used as the high molecular matrix. As the radically polymerizable monofunctional monomer, there can be exemplified unsaturated carboxylic acids such as acrylic acid, methacrylic acid and anhydrous maleic acid; acrylic and methacrylic ester compounds such as methyl acrylate, methyl methacrylate, benzyl methacrylate, phenyl methacrylate, and 2-hydroxyethyl methacrylate; fumaric ester compounds such as diethyl fumarate and diphenyl fumarate; thioacrylic and thiomethacrylic ester compounds such as methylthioacrylate, benzylthioacrylate and benzylthiomethacrylate; and vinyl compounds such as styrene, chlorostyrene, methylstyrene, vinylnaphthalene, α-methylstyrene dimer and bromostyrene.

There is no particular limitation on the method of dispersing the chromene compound of the present invention in the high molecular solid matrix, and any generally used method can be employed. For example, there can be employed a method of kneading the thermoplastic resin and the chromene compound together in a molten state and dispersing them in a resin, a method of dissolving the chromene compound in the polymerizable monomer, adding a polymerization catalyst thereto to conduct the polymerization with heat or light to disperse them in the resin, or a method of dispersing the chromene compound in the resin by dying the surfaces of the thermoplastic resin and the thermosetting resin with the chromene compound.

The chromene compound of the present invention can be extensively utilized as a photochromic material, such as various memory materials to replace for silver salt photosensitive materials, and various memory materials like a copying material, a photosensitive material for printing, a memory material for cathode-ray tubes, a photosensitive material for laser beams, and a photosensitive material for holography. Besides, the photochromic material using the chromene compound of the present invention can further be used as a photochromic lens material, an optical filter material, a display material, an actinometer and an ornamental material.

For example, the chromene compound can be used for the photochromic lenses without any particular limitation provided there is obtained a uniform dimming performance.

Concretely speaking, a polymer film in which the photochromic material of the invention is homogeneously dispersed is sandwiched in a lens, or the chromene compound of the invention is dispersed in the polymerizable monomer and is polymerized by a predetermined method, or the compound is dissolved in, for example, a silicone oil with which the lens surfaces are impregnated at 150 to 200° C. for 10 to 60 minutes, and the surfaces thereof are further coated with a curable material to obtain a photochromic lens.

Further, a coating agent comprising a polymerizable and curable composition which contains the chromene compound of the present invention may be applied onto the surfaces of the lens material and may, then, be cured. In this case, the lens material may have been treated for its surfaces relying upon a surface treatment using an alkaline solution or relying upon a plasma treatment, and may further be applied with a primer to improve the adhesion between the lens material and the coating (in combination with the surface treatment or without effecting the surface treatment).

EXAMPLES

The invention will be described in further detail by way of Examples to which only, however, the invention is in no way limited.

Example 1

1.0 Gram (0.0020 mols) of a 5-hydroxy-(7H)benzo(c)fluorene derivative of the following formula,

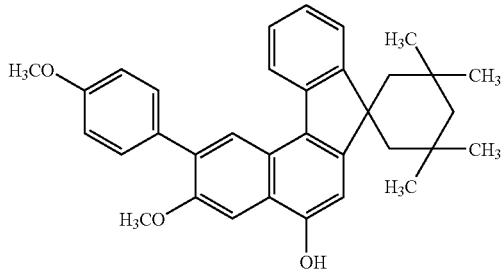

and 1.1 g (0.003 mols) of a propargyl alcohol derivative of the following formula,

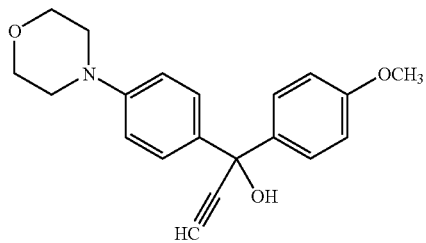

were dissolved in 70 ml of toluene to which was further added 0.020 g of a p-toluenesulfonic acid, and the mixture was stirred for one hour while being heated and refluxed. After the reaction, the solvent was removed and the residue was refined by chromatography on silica gel to obtain 1.1 g of a green powdery product. The yield was 70%.

The product was elementally analyzed to be C: 81.23%, H: 6.92%, N: 1.81%, O: 10.04%, which were in very good agreement with the calculated values (C: 81.27%, H: 6.95%, N: 1.76%, O: 10.02%) of $C_{54}H_{55}NO_5$.

Measurement of proton nuclear magnetic resonance spectra indicated, as shown in FIG. 1, peaks of 18H near δ: 1.0 to 3.0 ppm based on methyl and methylene proton of a tetramethylcyclohexane ring, peaks of 17H near near δ: 3.0 to 4.0 ppm based on methylene proton of morpholino group and on methyl proton of a methoxy group, and peaks of 20H near δ: 5.6 to 9.0 ppm based on an aromatic proton and a proton of an alkene.

Further, measurement of $^{13}C$-nuclear magnetic resonance spectra indicated a peak near δ: 110 to 160 ppm based on a carbon atom of an aromatic ring, a peak near δ: 80 to 140 ppm based on a carbon atom of an alkene, and a peak at δ: 20 to 60 ppm based on a carbon atom of an alkyl.

From the above results, it was confirmed that the isolated product was a compound represented by the following structural formula,

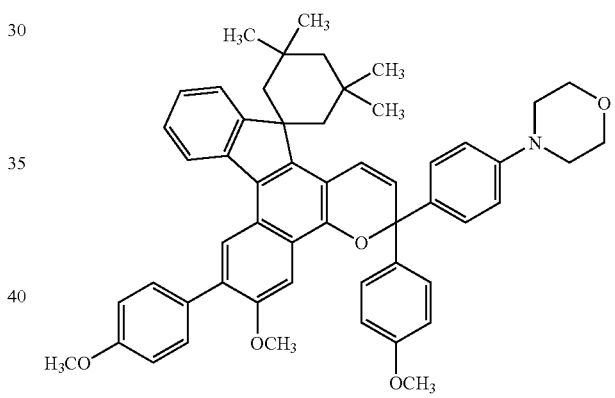

Examples 2 to 41

Chromene compounds shown in Tables 1, 2, 3, 4, 5, 6, 7, 8, 9 and 10 were synthesized in the same manner as in Example 1. The obtained products were analyzed for their structures relying on the same structure confirmation means as that of Example 1 to confirm that the compounds possessed the structural formulas as shown in Tables 1, 2, 3, 4, 5, 6, 7, 8, 9 and 10. Tables 11, 12 and 13 show elementally analyzed values of these compounds, values calculated from the structural formulas of the compounds, and characteristic spectra in the $^1$H-NMR spectra.

In the chemical formulas in Tables below, Me represents the methyl group and Et represents the ethyl group.

TABLE 1

| Ex. No. | Starting material | |
|---|---|---|
| | Benzofluorene derivative | Propargyl alcohol derivative |
| 2 | | |
| 3 | | |
| 4 | | |
| 5 | | |

| Ex. No. | Product | Yield (%) |
|---|---|---|

TABLE 1-continued
| 2 | 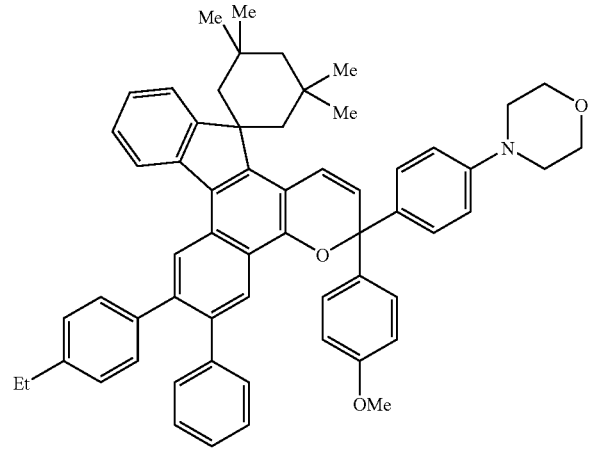 | 48 |
| 3 | 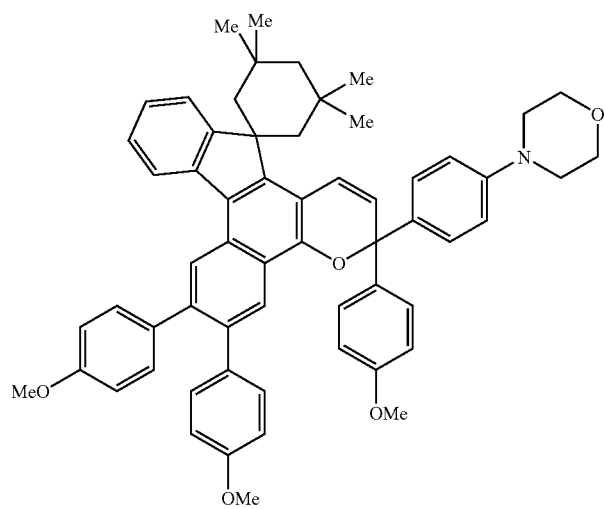 | 28 |
| 4 | 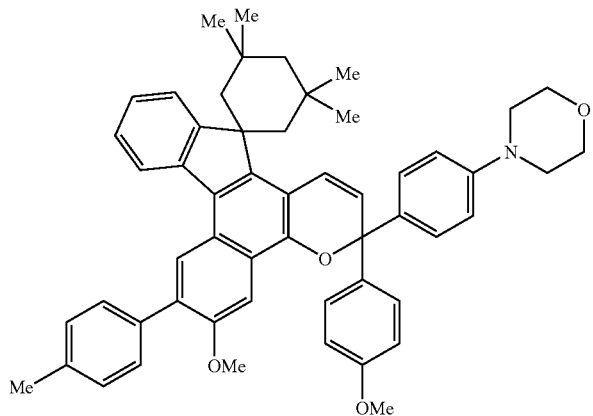 | 43 |

TABLE 1-continued
| 5 | 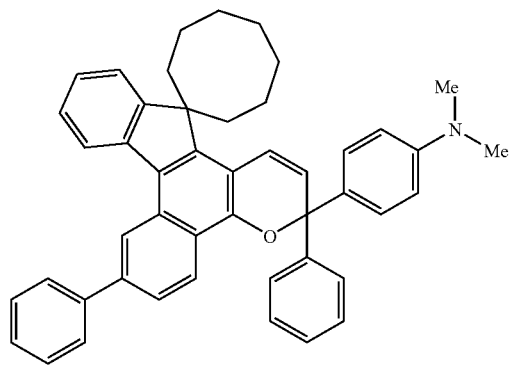 | 62 |
TABLE 2
| Ex. No. | Starting material | |
|---|---|---|
| | Benzofluorene derivative | Propargyl alcohol derivative |
| 6 | 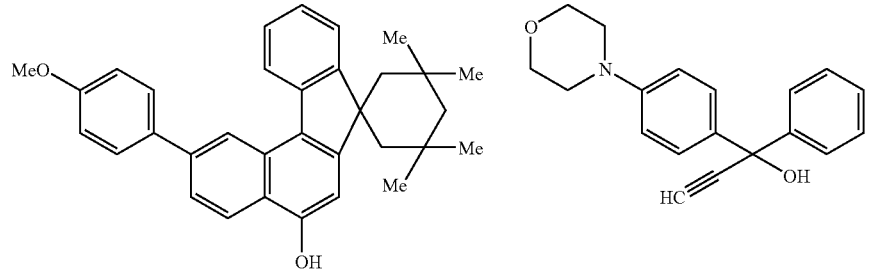 | |
| 7 | 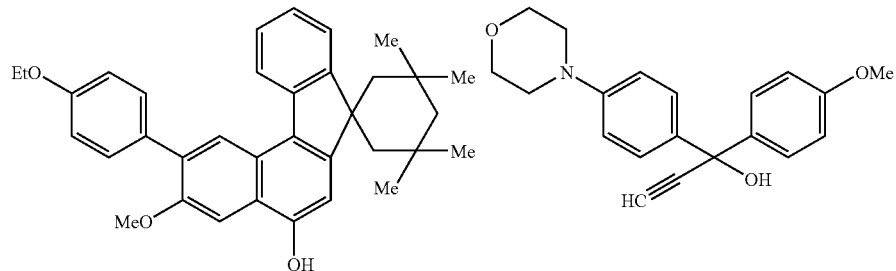 | |
| 8 | 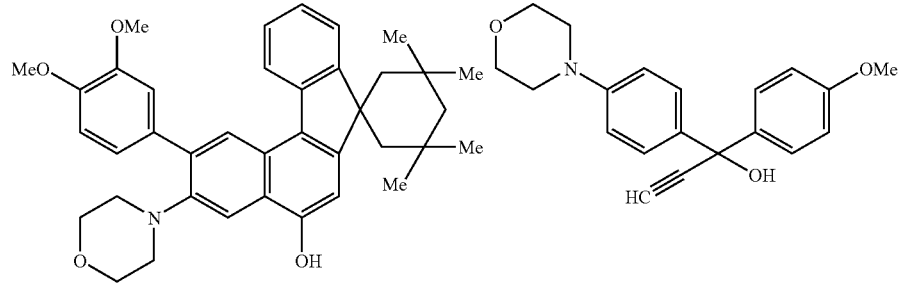 | |

TABLE 2-continued
| 9 | 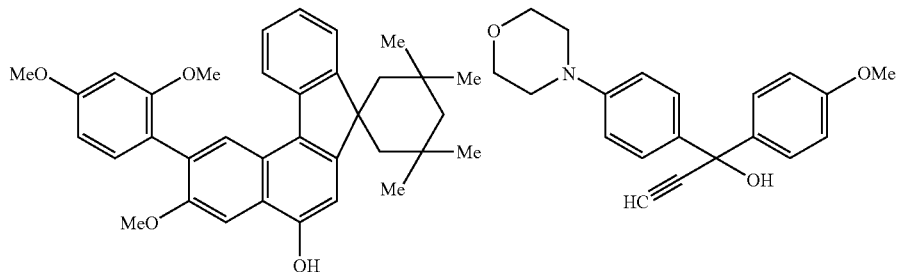 | |
| Ex. No. | Product | Yield (%) |
|---|---|---|
| 6 | 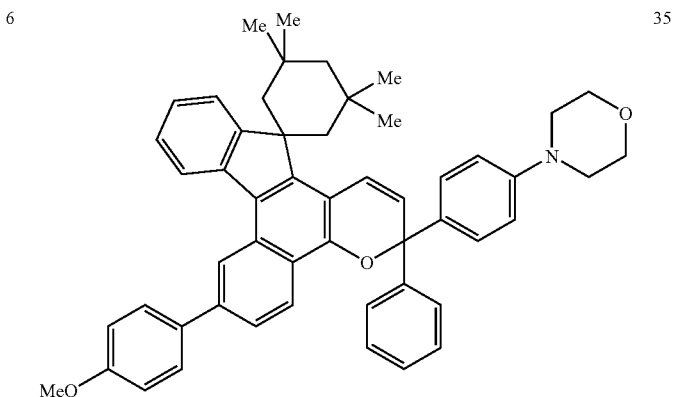 | 35 |
| 7 | 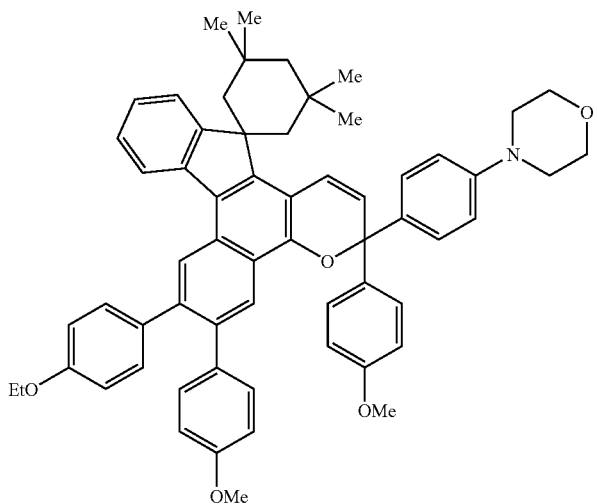 | 42 |

TABLE 2-continued

| 8 | [structure] | 38 |
| 9 | [structure] | 35 |

TABLE 3

| Ex. No. | Starting material | |
|---|---|---|
| | Benzofluorene derivative | Propargyl alcohol derivative |
| 10 | [structure] | [structure] |
| 11 | [structure] | [structure] |

TABLE 3-continued
| 12 | 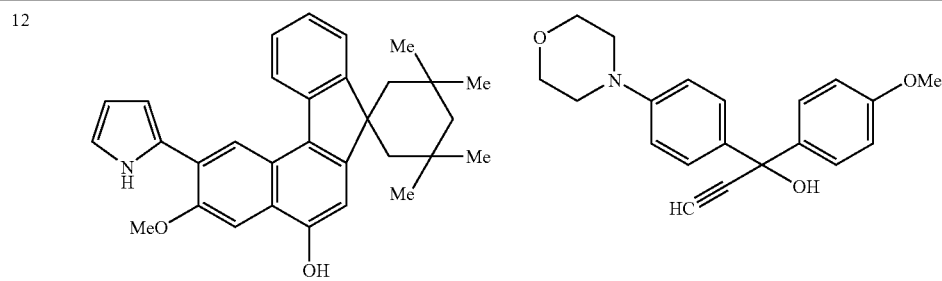 |
| --- | --- |
| 13 | 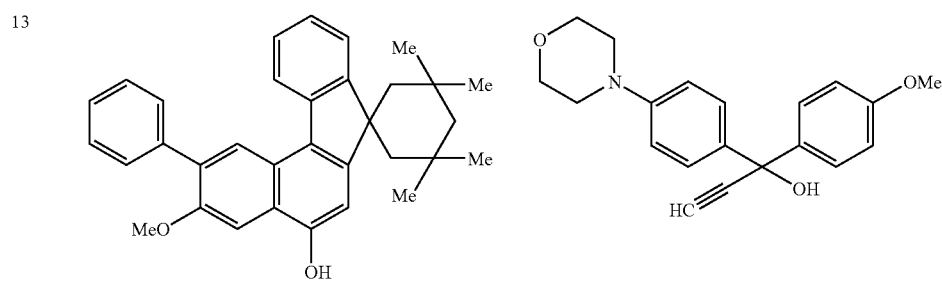 |
| Ex. No. | Product | Yield (%) |
| --- | --- | --- |
| 10 | 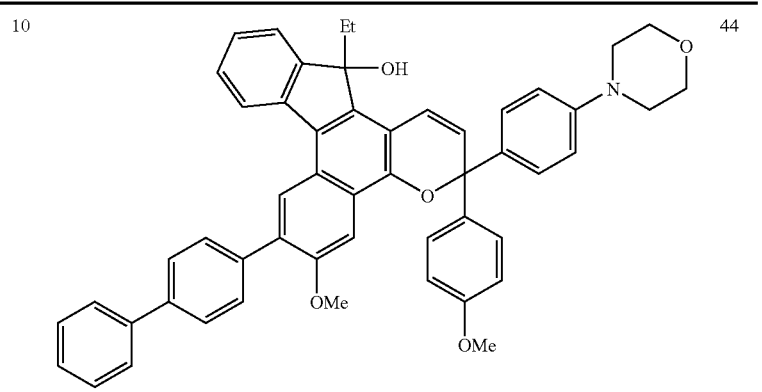 | 44 |
| 11 | 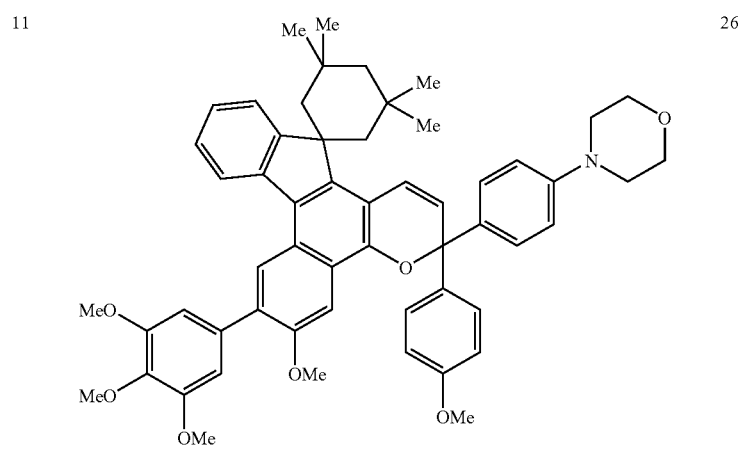 | 26 |

TABLE 3-continued

| 12 | [structure] | 38 |
| 13 | [structure] | 47 |

TABLE 4

| Ex. No. | Starting material | |
|---|---|---|
| | Benzofluorene derivative | Propargyl alcohol derivative |
| 14 | [structure] | [structure] |
| 15 | [structure] | [structure] |

TABLE 4-continued
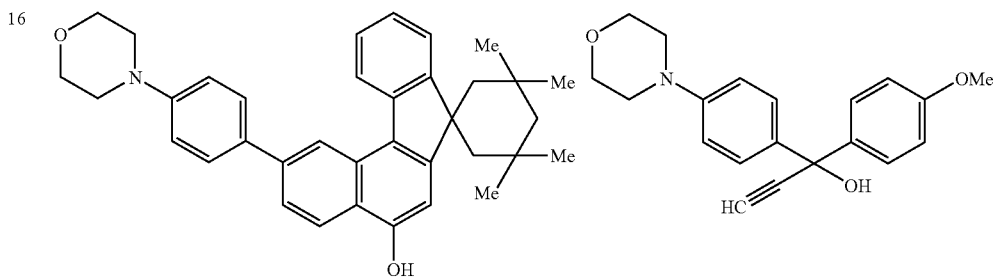
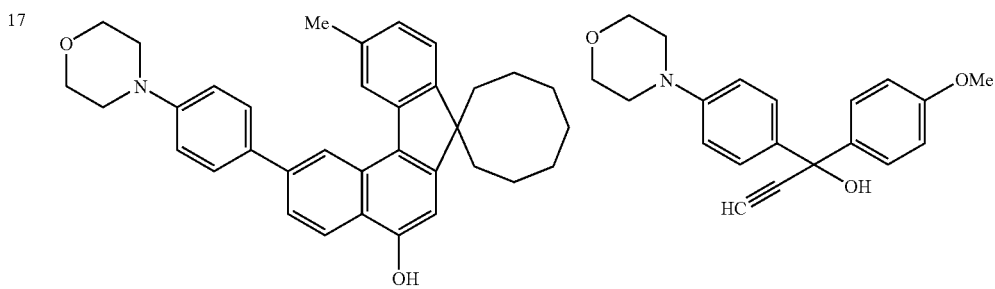
| Ex. No. | Product | Yield (%) |
|---|---|---|
| 14 | 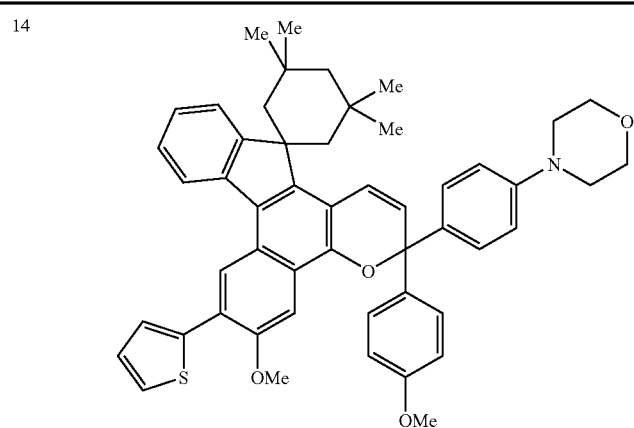 | 25 |
| 15 | 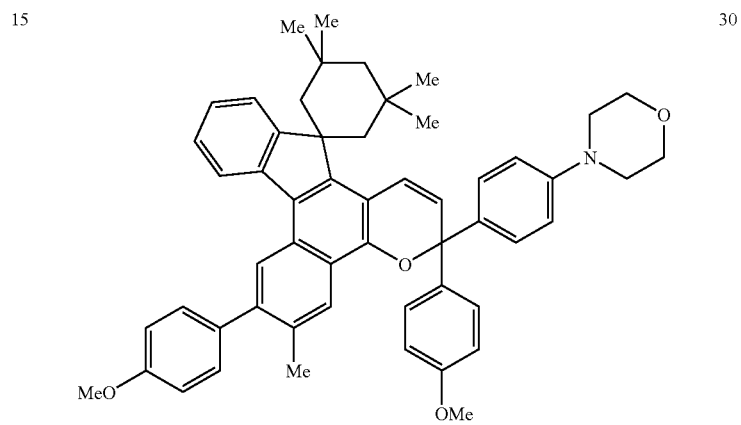 | 30 |

TABLE 4-continued
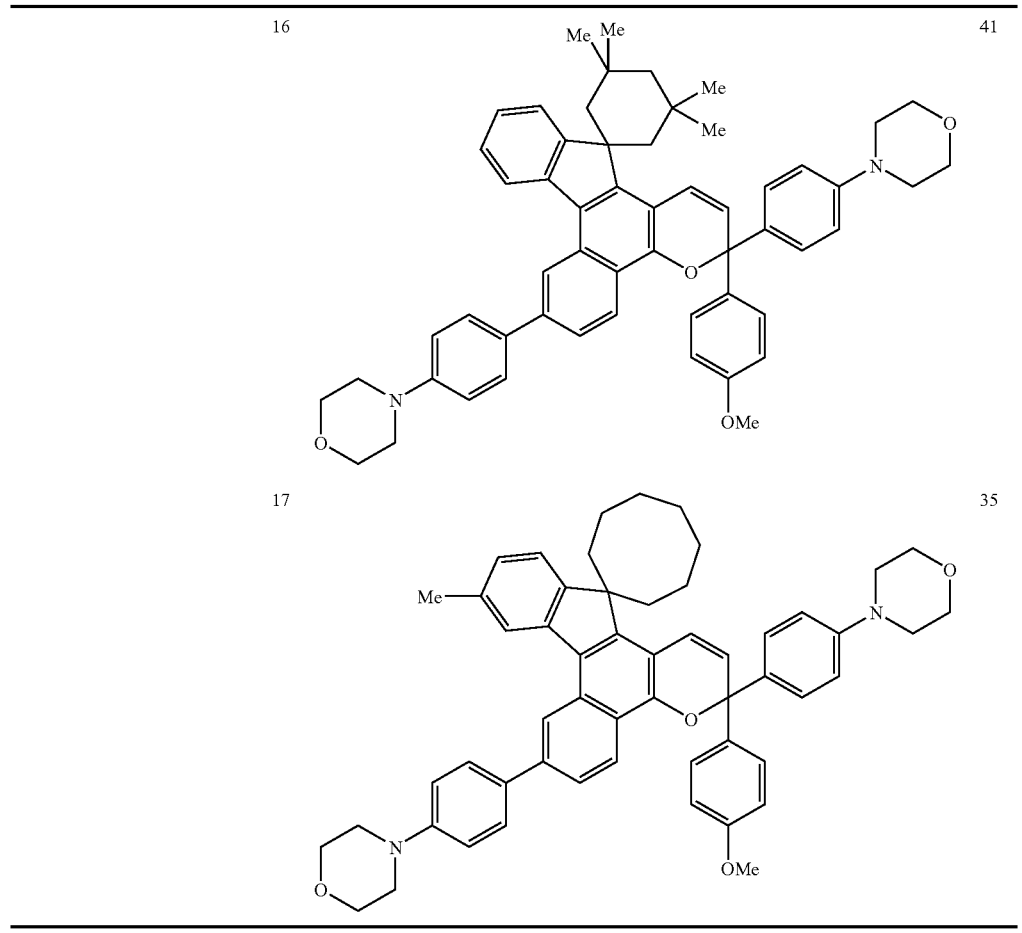
TABLE 5
| Ex. No. | Starting material | |
|---|---|---|
| | Benzofluorene derivative | Propargyl alcohol derivative |
| 18 | | |
| 19 | | |

TABLE 5-continued
| 20 | 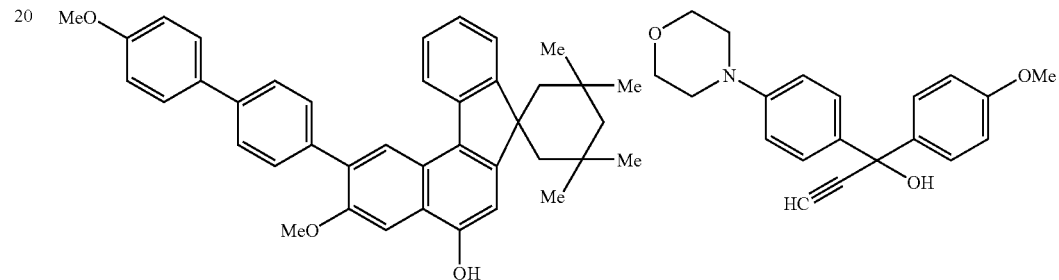 |
| --- | --- |
| 21 | 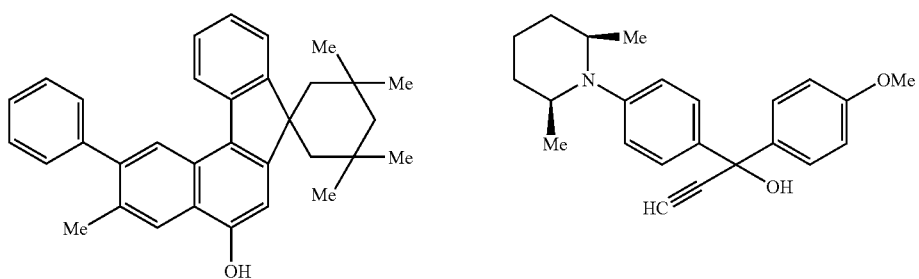 |
| Ex. No. | Product | Yield (%) |
| --- | --- | --- |
| 18 | 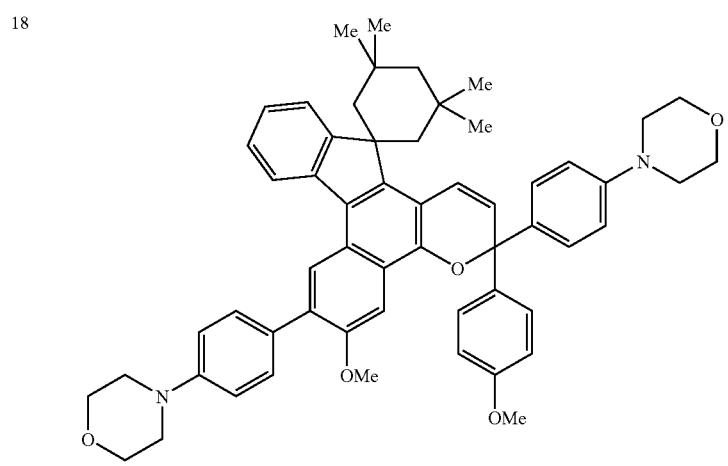 | 21 |
| 19 | 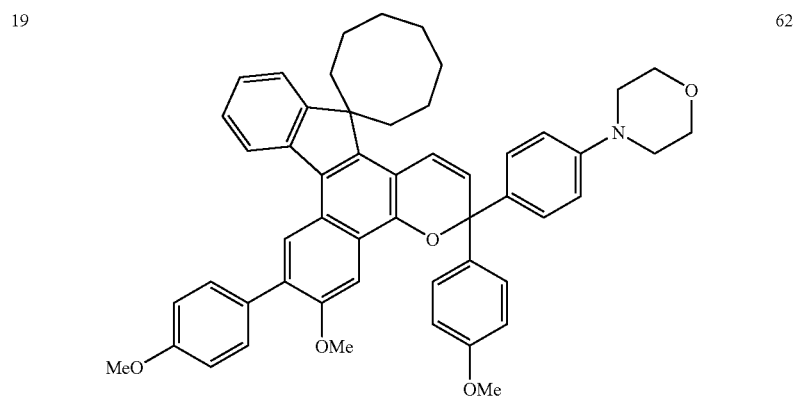 | 62 |

TABLE 5-continued
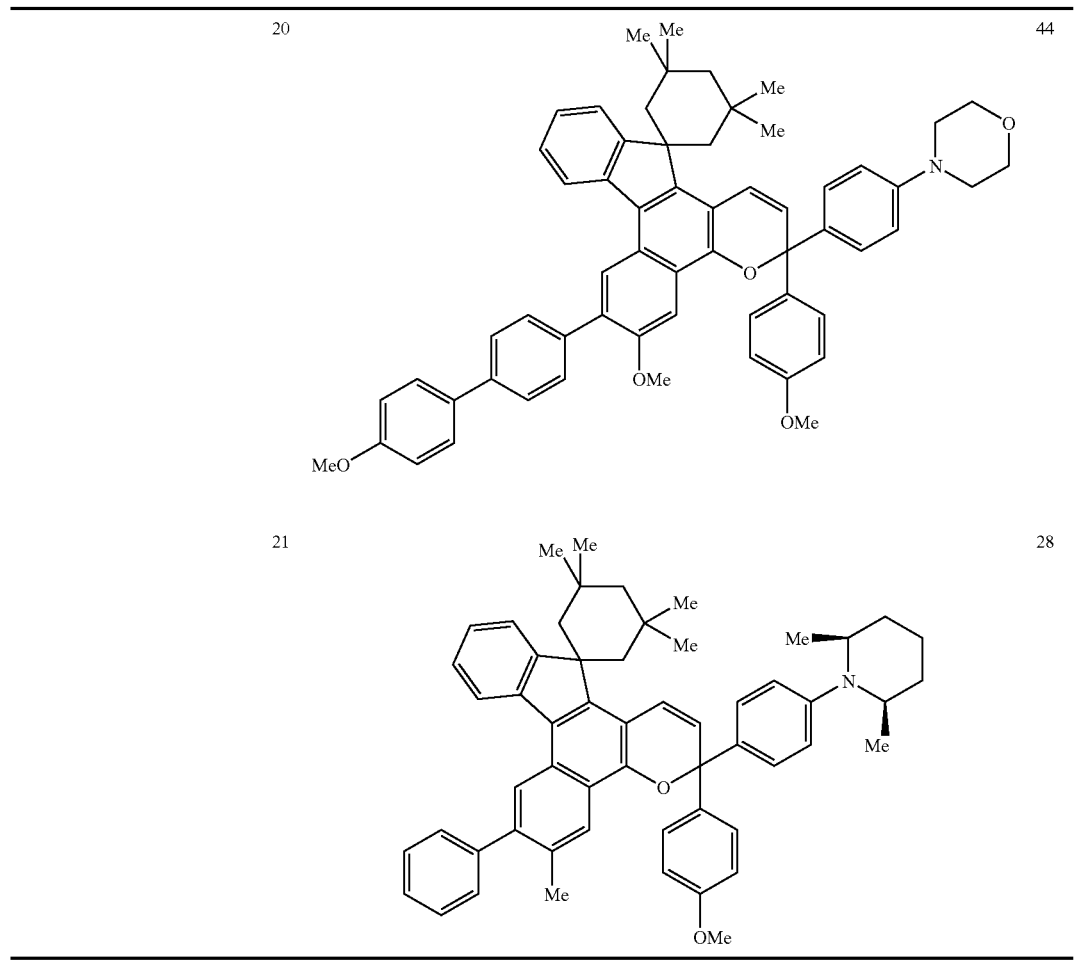
TABLE 6
| Ex. | Starting material | |
|---|---|---|
| No. | Benzofluorene derivative | Propargyl alcohol derivative |
| 22 | | |
| 23 | | |

TABLE 6-continued
| 24 | 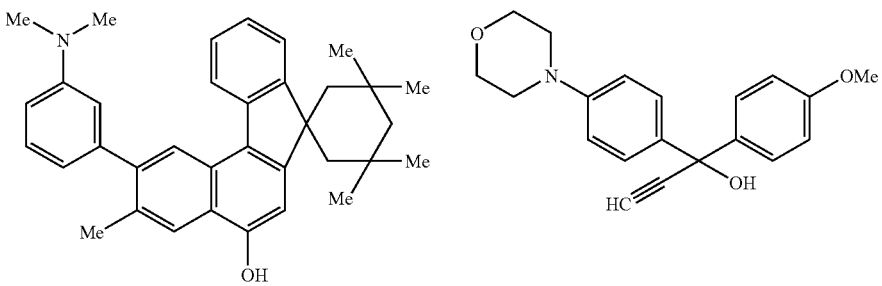 | | |
|---|---|---|---|
| 25 | 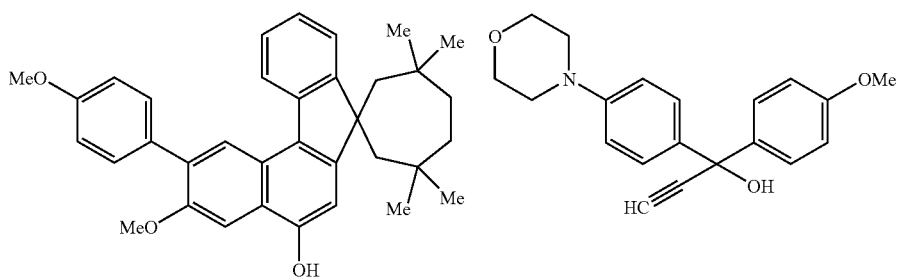 | | |
| Ex. No. | Product | Yield (%) |
|---|---|---|
| 22 | 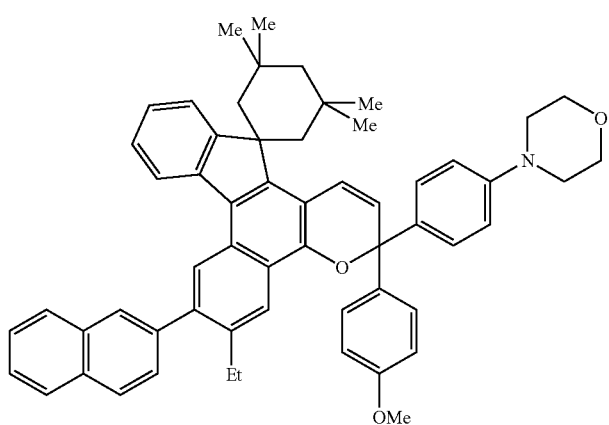 | 40 |
| 23 | 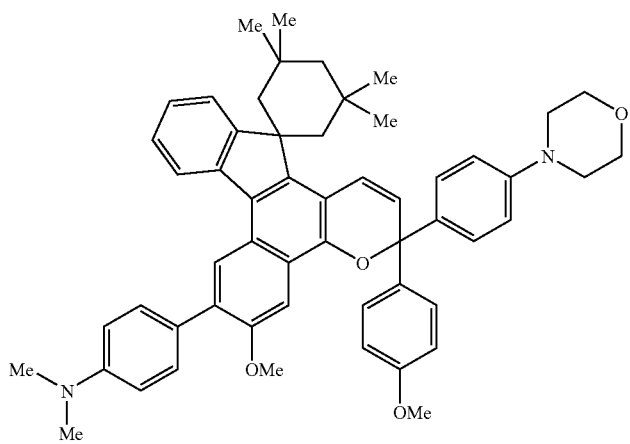 | 42 |

TABLE 6-continued
| 24 | 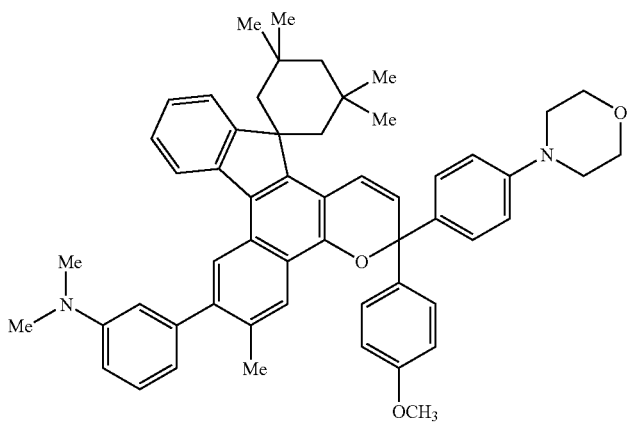 | 36 |
| 25 | 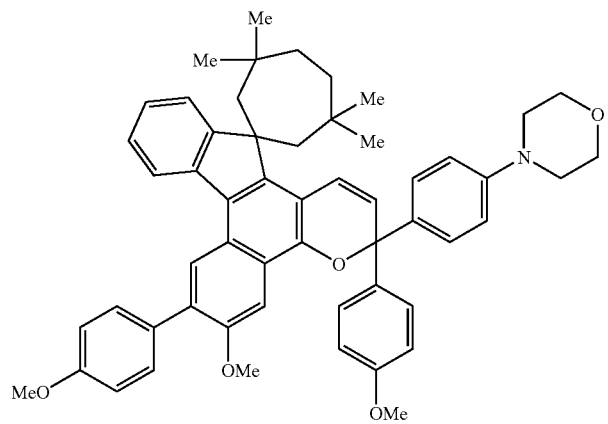 | 32 |
TABLE 7
| Ex. No. | Starting material | |
|---|---|---|
| | Benzofluorene derivative | Propargyl alcohol derivative |
| 26 | 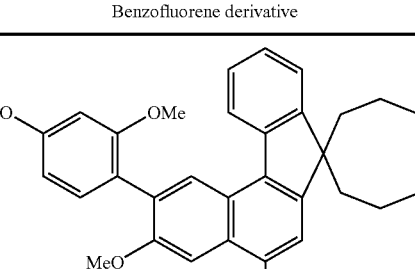 | 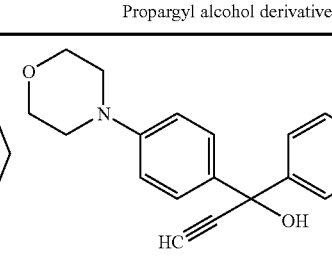 |
| 27 | 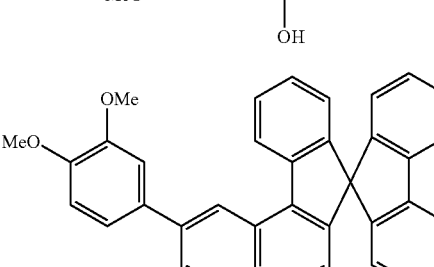 | 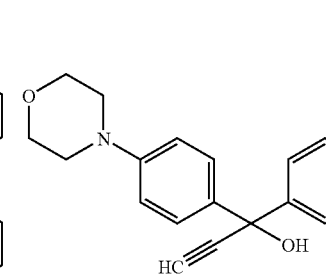 |

TABLE 7-continued
28 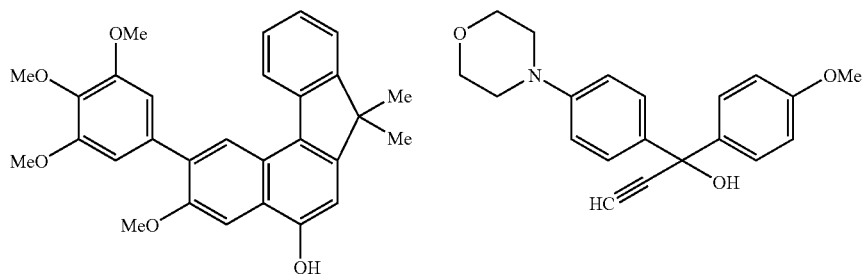
29 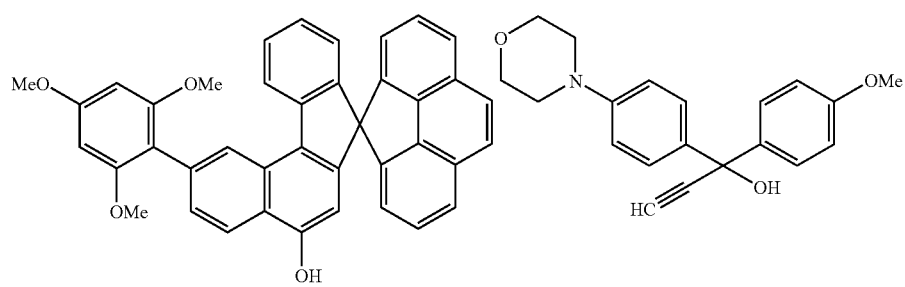
| Ex. No. | Product | Yield (%) |
|---|---|---|
| 26 | 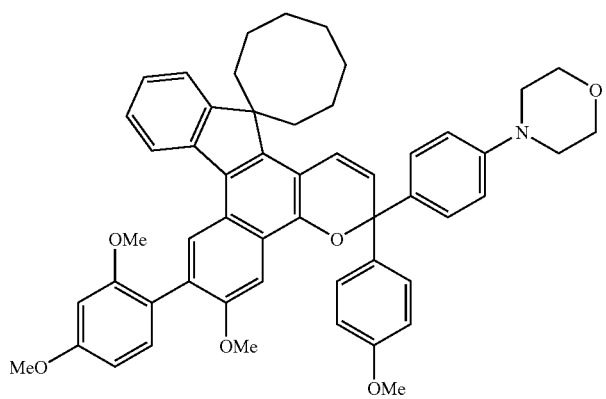 | 40 |
| 27 | 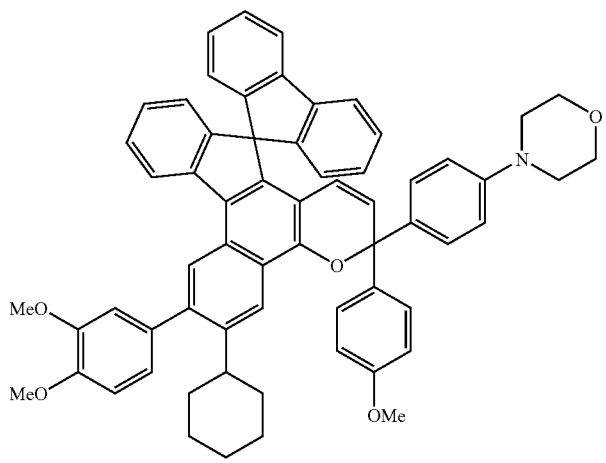 | 43 |

TABLE 7-continued
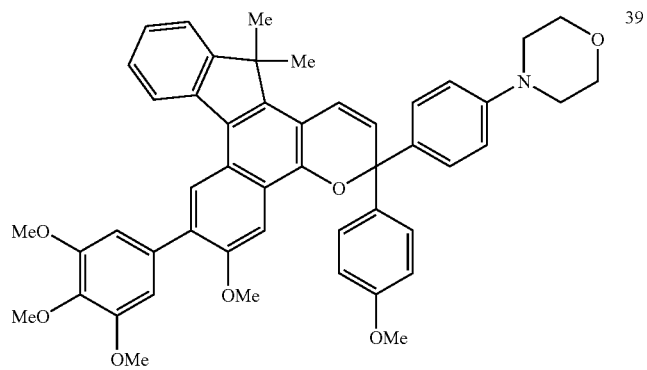
TABLE 8
| Ex. | Starting material | |
|---|---|---|
| No. | Benzofluorene derivative | Propargyl alcohol derivative |
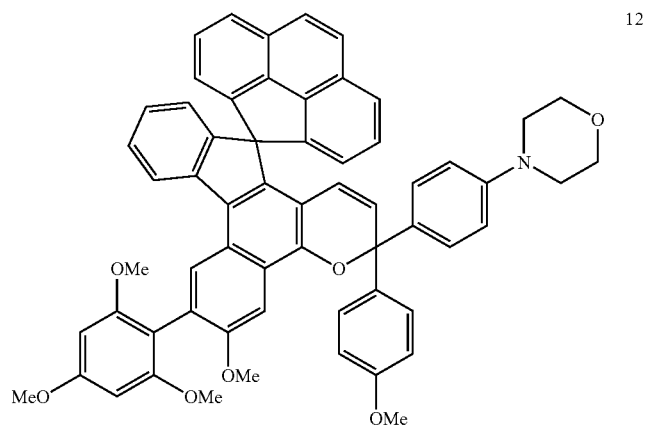

TABLE 8-continued
| 32 | 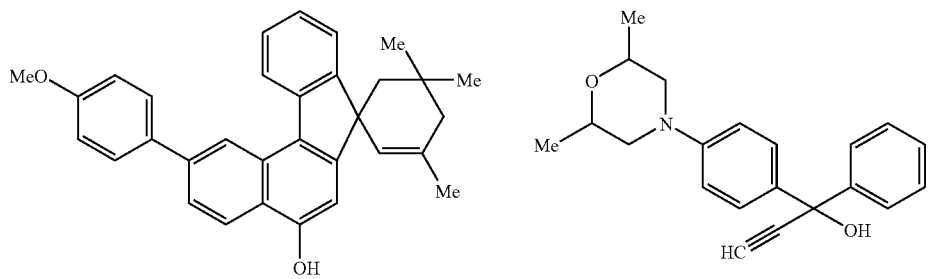 | |
| 33 | 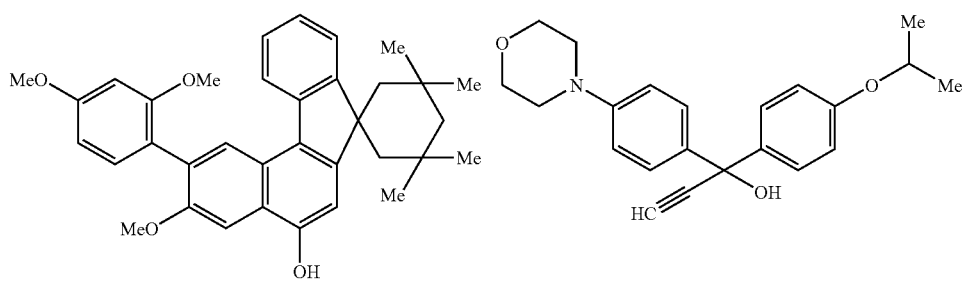 | |
| Ex. No. | Product | Yield (%) |
|---|---|---|
| 30 | 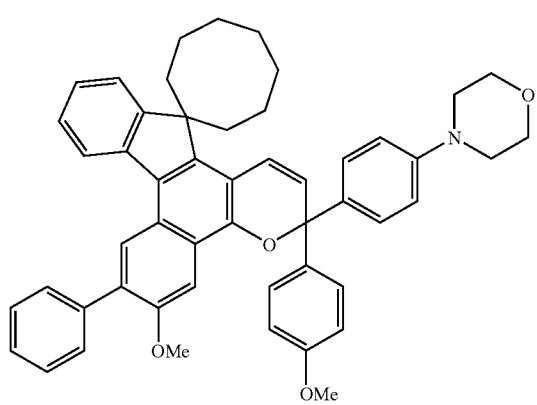 | 54 |
| 31 | 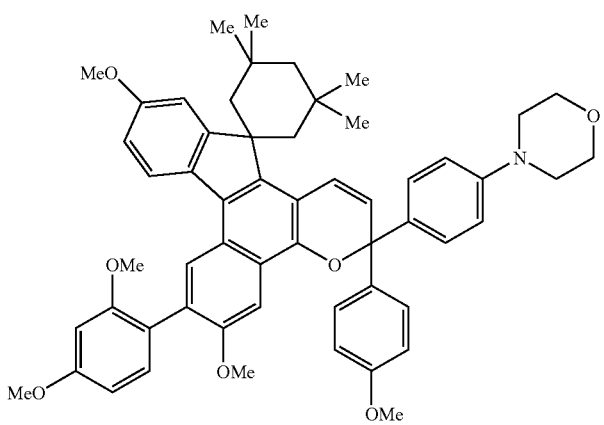 | 32 |

TABLE 8-continued
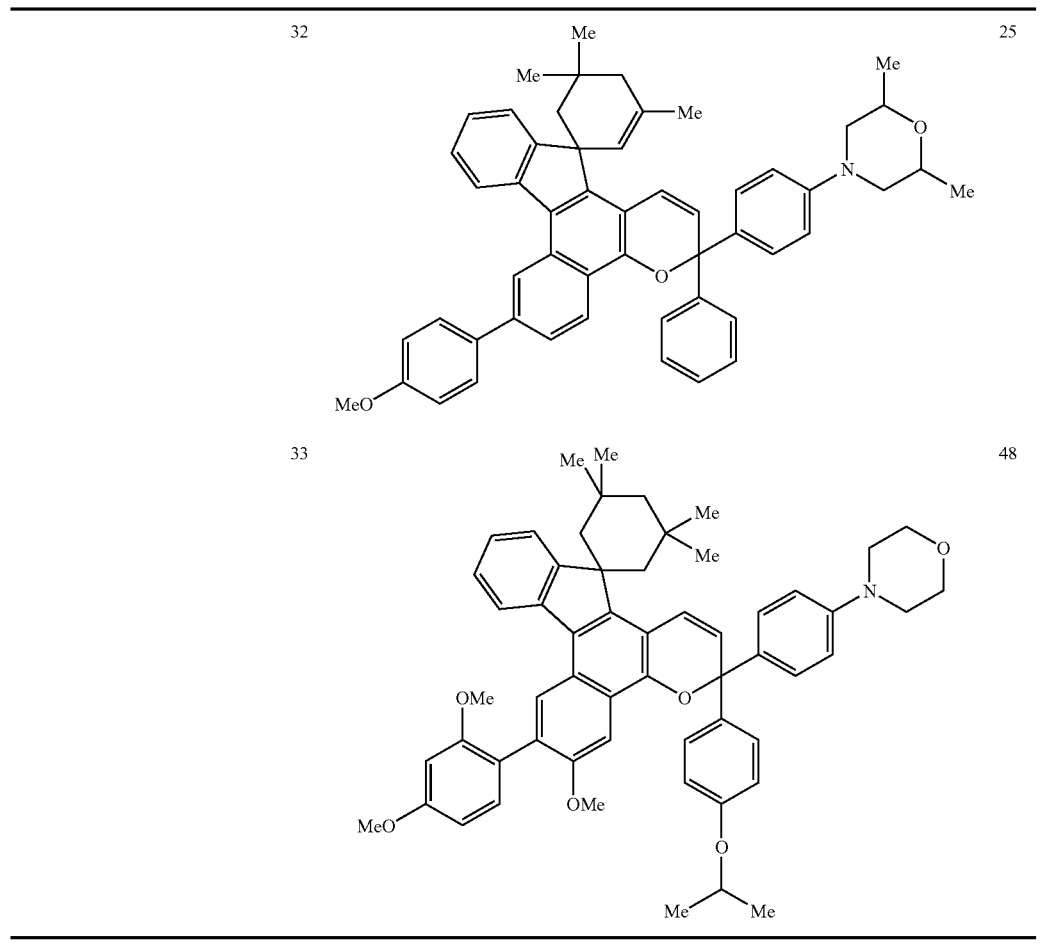
TABLE 9
| Ex. | Starting material | |
|---|---|---|
| No. | Benzofluorene derivative | Propargyl alcohol derivative |
| 34 | | |
| 35 | | |

TABLE 9-continued
| 36 | 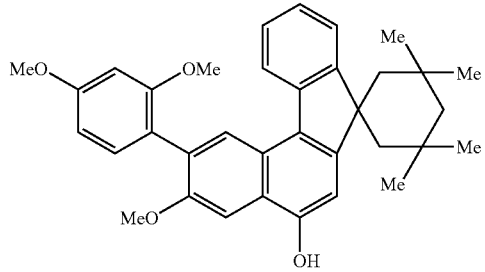 | 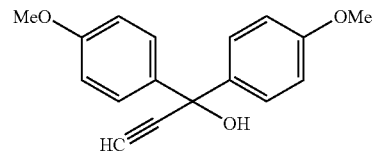 |
| 37 | 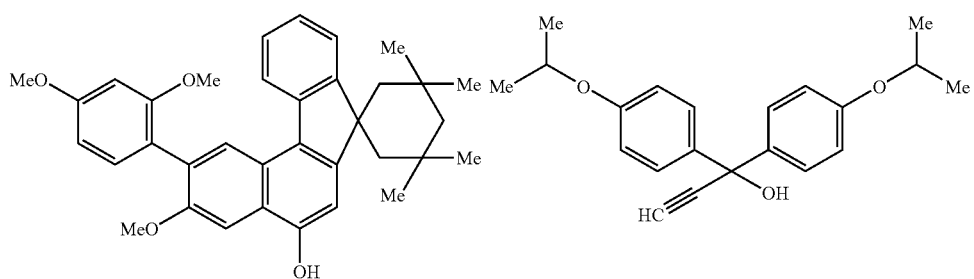 | |
| Ex. No. | Product | Yield (%) |
| --- | --- | --- |
| 34 | 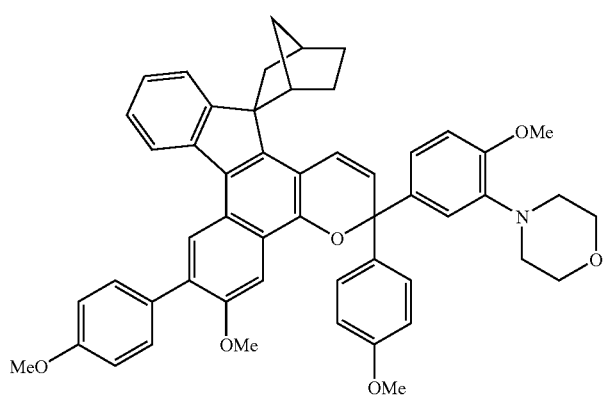 | 18 |
| 35 | 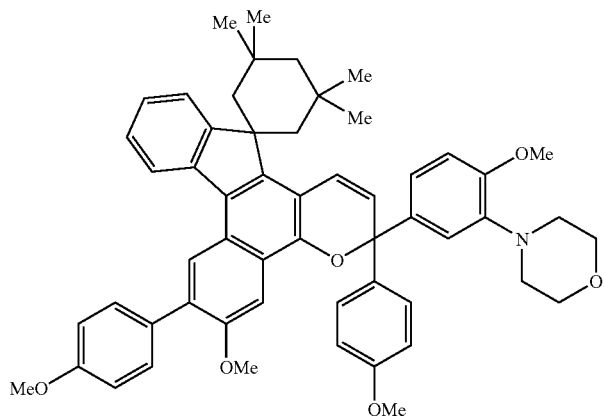 | 20 |

TABLE 9-continued

| 36 | (structure) | 25 |
| 37 | (structure) | 48 |

TABLE 10

| Ex. | Starting material | |
|---|---|---|
| No. | Benzofluorene derivative | Propargyl alcohol derivative |
| 38 | (structure) | (structure) |
| 39 | (structure) | (structure) |

TABLE 10-continued
| 40 | 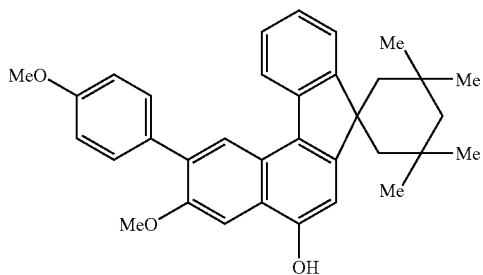 | 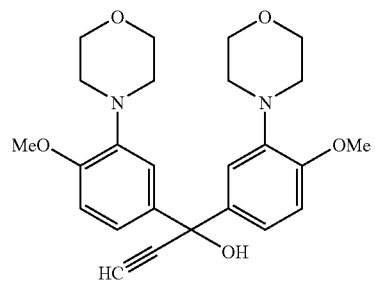 |
| --- | --- | --- |
| 41 | 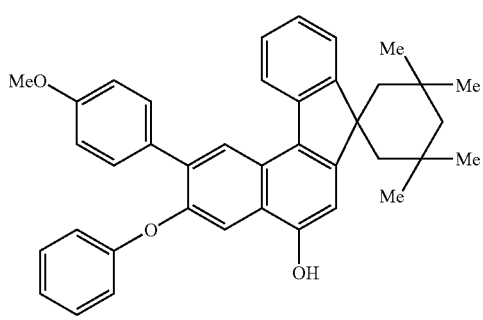 | 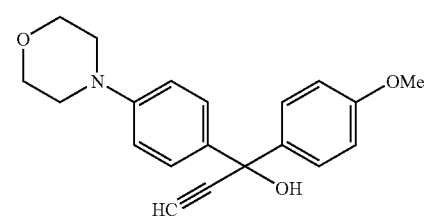 |
| Ex. No. | Product | Yield (%) |
| --- | --- | --- |
| 38 | 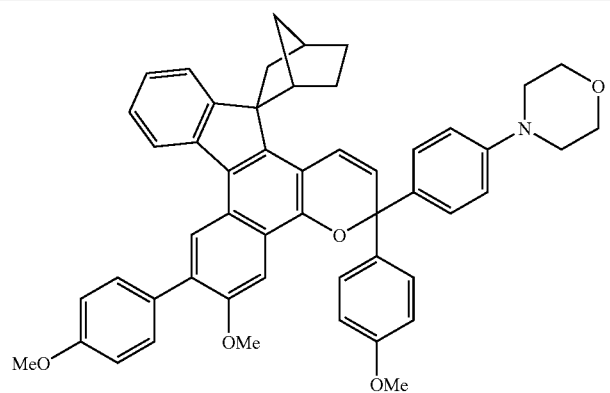 | 32 |
| 39 | 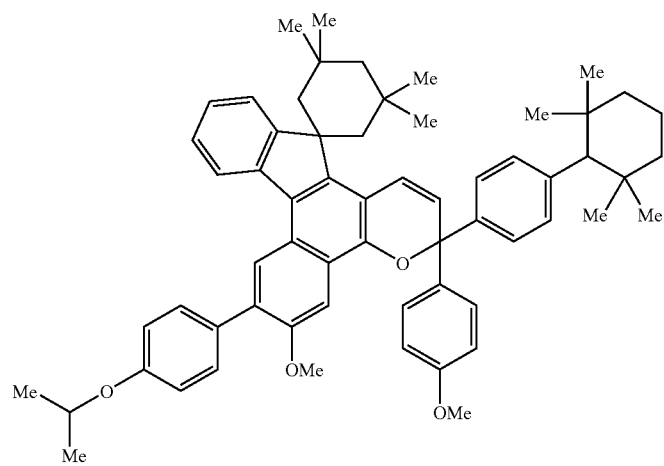 | 20 |

TABLE 10-continued
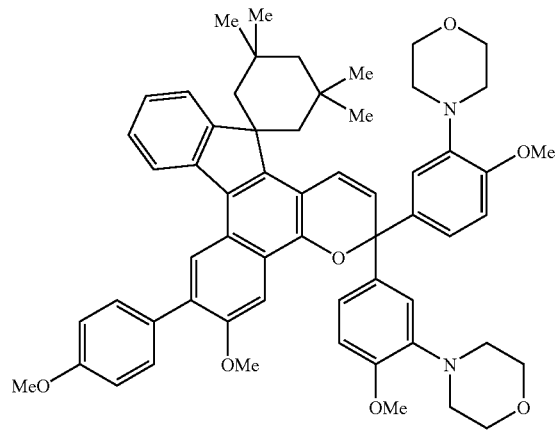
40
5
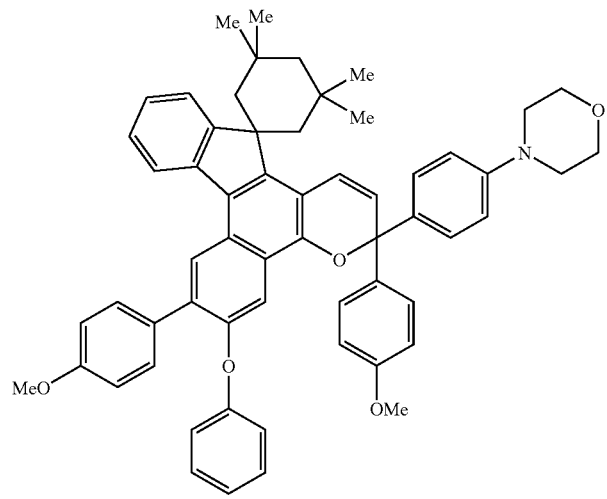
41
15
TABLE 11
| Ex. No. | Found | | | | | Calculated | | | | | $^1$H-NMR(ppm) |
|---|---|---|---|---|---|---|---|---|---|---|---|
| | C | H | N | O | S | C | H | N | O | S | |
| 2 | 85.49 | 7.12 | 1.72 | 5.67 | 0.00 | 85.58 | 7.06 | 1.66 | 5.70 | 0.00 | δ5.6~9.0:25H<br>δ1.5~4.5:34H |
| 3 | 82.41 | 6.80 | 1.63 | 9.16 | 0.00 | 82.44 | 6.80 | 1.60 | 9.15 | 0.00 | δ5.6~9.0:24H<br>δ1.5~4.5:35H |
| 4 | 82.88 | 7.02 | 1.85 | 8.25 | 0.00 | 82.94 | 7.09 | 1.79 | 8.18 | 0.00 | δ5.6~9.0:20H<br>δ1.5~4.5:35H |
| 5 | 88.48 | 6.75 | 2.20 | 2.57 | 0.00 | 88.50 | 6.79 | 2.20 | 2.51 | 0.00 | δ5.6~9.0:22H<br>δ1.5~4.5:21H |
| 6 | 84.58 | 7.01 | 1.93 | 6.48 | 0.00 | 84.63 | 6.97 | 1.90 | 6.50 | 0.00 | δ5.6~9.0:22H<br>δ1.5~4.5:29H |
| 7 | 81.42 | 7.12 | 1.73 | 9.73 | 0.00 | 81.35 | 7.08 | 1.72 | 9.85 | 0.00 | δ5.6~9.0:20H<br>δ1.5~4.5:37H |
| 8 | 78.79 | 7.13 | 3.09 | 10.99 | 0.00 | 78.88 | 7.08 | 3.17 | 10.87 | 0.00 | δ5.6~9.0:19H<br>δ1.5~4.5:43H |
| 9 | 79.80 | 6.95 | 1.68 | 11.57 | 0.00 | 79.78 | 6.94 | 1.69 | 11.59 | 0.00 | δ5.6~9.0:19H<br>δ1.5~4.5:38H |
| 10 | 81.67 | 5.98 | 1.83 | 10.52 | 0.00 | 81.76 | 5.94 | 1.83 | 10.47 | 0.00 | δ5.6~9.0:24H<br>δ1.5~4.5:21H |
| 11 | 78.38 | 6.92 | 1.63 | 13.07 | 0.00 | 78.39 | 6.93 | 1.63 | 13.05 | 0.00 | δ5.6~9.0:18H<br>δ1.5~4.5:41H |
| 12 | 80.78 | 7.01 | 3.72 | 8.49 | 0.00 | 80.92 | 6.92 | 3.70 | 8.45 | 0.00 | δ5.6~9.0:20H<br>δ1.5~4.5:32H |
| 13 | 82.89 | 6.97 | 1.80 | 8.34 | 0.00 | 82.89 | 6.96 | 1.82 | 8.33 | 0.00 | δ5.6~9.0:22H<br>δ1.5~4.5:31H |

TABLE 11-continued

| Ex. No. | Found | | | | | Calculated | | | | | ¹H-NMR(ppm) |
|---|---|---|---|---|---|---|---|---|---|---|---|
| | C | H | N | O | S | C | H | N | O | S | |
| 14 | 79.10 | 6.57 | 1.86 | 8.31 | 4.16 | 79.14 | 6.64 | 1.81 | 8.27 | 4.14 | δ5.6~9.0:19H δ1.5~4.5:32H |
| 15 | 82.99 | 7.06 | 1.75 | 8.20 | 0.00 | 82.94 | 7.09 | 1.79 | 8.18 | 0.00 | δ5.6~9.0:20H δ1.5~4.5:35H |

TABLE 12

| Ex. No. | Found | | | | | Calculated | | | | | ¹H-NMR(ppm) |
|---|---|---|---|---|---|---|---|---|---|---|---|
| | C | H | N | O | S | C | H | N | O | S | |
| 16 | 81.70 | 7.10 | 3.42 | 7.78 | 0.00 | 81.72 | 7.10 | 3.40 | 7.78 | 0.00 | δ5.6~9.0:21H δ1.5~4.5:37H |
| 17 | 81.57 | 6.87 | 3.52 | 8.04 | 0.00 | 81.65 | 6.98 | 3.46 | 7.91 | 0.00 | δ5.6~9.0:20H δ1.5~4.5:36H |
| 18 | 80.23 | 7.06 | 3.31 | 9.40 | 0.00 | 80.25 | 7.09 | 3.28 | 9.38 | 0.00 | δ5.6~9.0:20H δ1.5~4.5:40H |
| 19 | 81.10 | 6.68 | 1.84 | 10.38 | 0.00 | 81.11 | 6.68 | 1.82 | 10.39 | 0.00 | δ5.6~9.0:20H δ1.5~4.5:31H |
| 20 | 82.38 | 6.73 | 1.72 | 9.17 | 0.00 | 82.44 | 6.80 | 1.60 | 9.15 | 0.00 | δ5.6~9.0:24H δ1.5~4.5:35H |
| 21 | 86.53 | 7.77 | 1.72 | 3.98 | 0.00 | 86.44 | 7.64 | 1.80 | 4.11 | 0.00 | δ5.6~9.0:21H δ1.5~4.5:38H |
| 22 | 85.23 | 7.09 | 1.78 | 5.90 | 0.00 | 85.36 | 7.04 | 1.72 | 5.88 | 0.00 | δ5.6~9.0:23H δ1.5~4.5:34H |
| 23 | 81.38 | 7.24 | 3.51 | 7.87 | 0.00 | 81.45 | 7.21 | 3.45 | 7.89 | 0.00 | δ5.6~9.0:20H δ1.5~4.5:38H |
| 24 | 83.18 | 7.28 | 3.65 | 5.89 | 0.00 | 83.09 | 7.35 | 3.52 | 6.04 | 0.00 | δ5.6~9.0:20H δ1.5~4.5:38H |
| 25 | 81.27 | 7.15 | 1.69 | 9.89 | 0.00 | 81.35 | 7.08 | 1.72 | 9.85 | 0.00 | δ5.6~9.0:20H δ1.5~4.5:37H |
| 26 | 79.58 | 6.65 | 1.74 | 12.03 | 0.00 | 79.57 | 6.68 | 1.75 | 12.00 | 0.00 | δ5.6~9.0:19H δ1.5~4.5:34H |
| 27 | 83.45 | 6.04 | 1.72 | 8.79 | 0.00 | 83.51 | 6.12 | 1.55 | 8.83 | 0.00 | δ5.6~9.0:27H δ1.5~4.5:28H |
| 28 | 77.18 | 6.30 | 1.78 | 14.74 | 0.00 | 77.24 | 6.22 | 1.84 | 14.70 | 0.00 | δ5.6~9.0:18H δ1.5~4.5:29H |
| 29 | 82.00 | 5.51 | 1.57 | 10.92 | 0.00 | 82.08 | 5.40 | 1.60 | 10.93 | 0.00 | δ5.6~9.0:26H δ1.5~4.5:23H |
| 30 | 82.77 | 6.66 | 1.89 | 8.68 | 0.00 | 82.78 | 6.67 | 1.89 | 8.65 | 0.00 | δ5.6~9.0:21H δ1.5~4.5:28H |

TABLE 13

| Ex. No. | Found | | | | | Calculated | | | | | ¹H-NMR(ppm) |
|---|---|---|---|---|---|---|---|---|---|---|---|
| | C | H | N | O | S | C | H | N | O | S | |
| 31 | 78.36 | 6.99 | 1.58 | 13.07 | 0.00 | 78.39 | 6.93 | 1.63 | 13.05 | 0.00 | δ5.6~9.0:18H δ1.5~4.5:41H |
| 32 | 84.92 | 6.85 | 1.89 | 8.04 | 6.34 | 84.88 | 6.85 | 1.87 | 6.40 | 0.00 | δ5.6~9.0:22H δ1.5~4.5:29H |
| 33 | 80.01 | 7.22 | 1.55 | 11.22 | 0.00 | 79.97 | 7.18 | 1.64 | 11.21 | 0.00 | δ5.6~9.0:19H δ1.5~4.5:42H |
| 34 | 79.53 | 6.66 | 1.81 | 12.00 | 0.00 | 79.57 | 6.68 | 1.75 | 12.00 | 0.00 | δ5.6~9.0:19H δ1.5~4.5:34H |
| 35 | 79.75 | 6.99 | 1.63 | 11.63 | 0.00 | 79.78 | 6.94 | 1.69 | 11.59 | 0.00 | δ5.6~9.0:19H δ1.5~4.5:38H |
| 36 | 80.75 | 6.78 | 0.00 | 12.47 | 0.00 | 80.80 | 6.78 | 0.00 | 12.42 | 0.00 | δ5.6~9.0:19H δ1.5~4.5:33H |
| 37 | 81.15 | 7.33 | 0.00 | 11.52 | 0.00 | 81.13 | 7.29 | 0.00 | 11.58 | 0.00 | δ5.6~9.0:19H δ1.5~4.5:41H |
| 38 | 81.16 | 6.66 | 1.85 | 10.33 | 0.00 | 81.11 | 6.68 | 1.82 | 10.39 | 0.00 | δ5.6~9.0:20H δ1.5~4.5:31H |
| 39 | 83.18 | 7.85 | 1.63 | 7.34 | 0.00 | 83.24 | 7.90 | 1.59 | 7.27 | 0.00 | δ5.6~9.0:20H δ1.5~4.5:49H |
| 40 | 77.54 | 7.10 | 3.01 | 12.35 | 0.00 | 77.60 | 7.06 | 3.07 | 12.26 | 0.00 | δ5.6~9.0:18H δ1.5~4.5:46H |
| 41 | 82.33 | 6.71 | 1.66 | 9.30 | 0.00 | 82.39 | 6.68 | 1.63 | 9.30 | 0.00 | δ5.6~9.0:24H δ1.5~4.5:33H |

Examples 42 to 82 and Comparative Examples 1 to 4

The chromene compound obtained in Example 1 was mixed with radically polymerizable monomers to prepare photochromic polymerizable compositions.

That is, to 100 parts by weight of a mixture of radically polymerizable monomers containing 2,2-bis(4-methacryloyloxypentaethoxyphenyl)propane/polyethylene glycol diacrylate (average molecular weight of 532)/trimethylolpropane trimethacrylate/polyester oligomer hexaacrylate (EB-1830 manufactured by Daicel UCB Co.)/glycidyl methacrylate at a weight ratio of 50 parts by weight/15 parts by weight/15 parts by weight/10 parts by weight/10 parts by weight, there was added 1 part by weight of a chromene compound obtained in Example 1 and was mixed to a sufficient degree, followed by the addition of:

1-hydroxycyclohexylphenylketone (polymerization initiator): 0.375 parts by weight, bis(2,6-dimethoxybenzoyl)-2,4,4'-trimethyl-pentylphosphineoxide (polymerization initiator): 0.125 parts by weight, bis(1,2,2,6,6-pentamethyl-4-piperidyl)sebacate (stabilizer): 5 parts by weight, γ-methacryloyloxypropyltrimethoxysilane (silane coupling agent): 7 parts by weight, and N-methyldiethanolamine (solvent): 3 parts by weight, and the mixture was mixed to a sufficient degree to prepare a photochromic polymerizable composition.

Next, about 2 g of the obtained photochromic polymerizable composition was spin-coated onto the surface of the lens material (CR39: allyl resin plastic lens, refractive index=1.50) by using a spin coater, 1H-DX2, manufactured by Mikasa Co. The lens of which the surface was coated was irradiated with light in a nitrogen gas atmosphere by using a metal halide lamp of a power of 120 mW/cm$^2$ for 3 minutes to cure the coating, followed by heating in a constant-temperature heater maintained at 120° C. to obtain a thin photochromic cured film.

The obtained thin photochromic cured film (film thickness of 30 μm) was irradiated with light by using a xenon lamp, L-2480(300W)SHL-100 manufactured by Hamamatsu Photonics Co. as a source of light through an aeromass filter (manufactured by Coning Co.) for 120 seconds under the following conditions to develop a color, and was evaluated for its photochromic properties.

<Light Irradiation Conditions>

Environmental temperature: 20° C.±1° C.

Beam intensity on the surface of the cured thin film:

365 nm; 2.4 mW/cm$^2$ 245 nm; 24 μW/cm$^2$

The photochromic properties were evaluated concerning the following properties.

(1) Maximum absorption wavelength (λmax): A maximum absorption wavelength after having developed color as found by using a spectrophotometer (instantaneous multichannel photodetector MCPD1000) manufactured by Otsuka Denshi Kogyo Co.

The maximum absorption wavelength is related to a color tone at the time of developing a color.

(2) Initial color {ε(0)}: Absorbancy at the maximum absorption wavelength in a state of not irradiated with light.

In an optical material such as a spectacle lens, it can be said that the lower this value, the more the photochromic properties are excellent.

(3) Color density {ε(120)−ε(0)}: A difference between the absorbancy {ε(120)} at the maximum absorption wavelength after irradiated with light for 120 seconds and the above ε(0).

It can be said that the higher this value, the more the photochromic properties are excellent.

(4) Yellow/blue ratio: A ratio of the maximum absorption wavelength in the yellow peripheral region and the maximum absorption wavelength in the blue peripheral region at the color density obtained in (3).

When this value is close to 1, it can be said that a high double peaking is exhibited.

(5) Color-developing sensitivity (sec.): A time until the absorbancy of the thin cured film which is the sample at the maximum wavelength reaches the saturation upon the irradiation with light.

It can be said that the shorter this time, the more excellent the color-developing sensitivity.

(6) Fading half-life [$t_{1/2}$ (min.)]: A time until the absorbancy of the sample at the maximum wavelength decreases down to one-half the [ε(120)−ε(0)] from when the sample is no longer irradiated with light after having been irradiated with light after it was irradiated with light for 120 seconds.

It can be said that the shorter this time, the more excellent the photochromic properties.

(7) Remaining Ratio (%)={($A_{50}/A_0$)×100}:

The following aging acceleration testing was conducted to evaluate the resistance of color developed by the irradiation with light.

That is, the obtained thin cured film was aged for 50 hours by using a xenon weather meter, X25, manufactured by Suga Shikenki Co. The color density was evaluated before and after the testing. The color density ($A_0$) before the testing and the color density ($A_{50}$) after the testing were measured, and a value {($A_{50}/A_0$)×100} was regarded to be the remaining ratio (%) and was used as an index of resistance of the developed color. The higher the remaining ratio, the higher the resistance of the developed color.

(8) Change in the coloring degree (ΔYI)=YI(50)−YI(0):

To evaluate the resistance of color tone of when not irradiated with light, the samples before and after the aging acceleration testing were measured for their color difference by using a color-difference meter (SM-4) manufactured by Suga Shikenki Co. A change in the coloring degree due to aging was found by finding a difference {ΔYI} which is obtained by subtracting a value {YI(0)} of the coloring degree of before the testing from a value {YI(50) of the coloring degree of after the testing, and the resistance was evaluated. The smaller the difference ΔYI, the higher the resistance of color tone of when not irradiated with light.

Further, thin cured films of the photochromic polymers were obtained in the same manner as described above but using the compounds obtained in Examples 2 to 41 as chromene compounds, and their properties were evaluated. The results were as shown in Tables 14, 15 and 16.

TABLE 14

| Ex. No. | Compound No. | $\lambda$max (nm) | Initial color $\epsilon(0)$ | Color density $\epsilon(120)-\epsilon(0)$ | Yellow/blue ratio | Color-developing sensitivity (sec.) | Fading half-life $\tau^{1/2}$ (min.) | Light resistance $\Delta$YI | Remaining ratio (%) |
|---|---|---|---|---|---|---|---|---|---|
| 42 | 1 | 474 | 0.03 | 0.41 | 0.82 | 55 | 1.4 | 1.8 | 75 |
|  |  | 592 | 0.03 | 0.50 |  |  | 1.4 |  | 75 |
| 43 | 2 | 466 | 0.03 | 0.35 | 0.69 | 65 | 1.8 | 1.8 | 75 |
|  |  | 570 | 0.03 | 0.51 |  |  | 1.8 |  | 75 |
| 44 | 3 | 475 | 0.03 | 0.36 | 0.69 | 60 | 1.6 | 1.7 | 74 |
|  |  | 588 | 0.03 | 0.52 |  |  | 1.6 |  | 74 |
| 45 | 4 | 472 | 0.03 | 0.39 | 0.78 | 60 | 1.6 | 1.8 | 72 |
|  |  | 588 | 0.03 | 0.50 |  |  | 1.6 |  | 72 |
| 46 | 5 | 474 | 0.03 | 0.32 | 0.71 | 60 | 2.0 | 2.2 | 67 |
|  |  | 585 | 0.03 | 0.45 |  |  | 2.0 |  | 67 |
| 47 | 6 | 471 | 0.04 | 0.31 | 0.60 | 55 | 1.4 | 1.7 | 69 |
|  |  | 582 | 0.04 | 0.52 |  |  | 1.4 |  | 69 |
| 48 | 7 | 476 | 0.03 | 0.43 | 0.86 | 55 | 1.3 | 1.8 | 75 |
|  |  | 598 | 0.03 | 0.50 |  |  | 1.3 |  | 75 |
| 49 | 8 | 466 | 0.05 | 0.72 | 1.20 | 60 | 1.3 | 2.3 | 70 |
|  |  | 575 | 0.05 | 0.60 |  |  | 1.3 |  | 70 |
| 50 | 9 | 472 | 0.04 | 0.52 | 1.00 | 65 | 1.1 | 1.2 | 73 |
|  |  | 588 | 0.04 | 0.52 |  |  | 1.1 |  | 73 |
| 51 | 10 | 471 | 0.03 | 0.51 | 0.85 | 55 | 3.5 | 2.4 | 62 |
|  |  | 588 | 0.03 | 0.60 |  |  | 3.5 |  | 62 |
| 52 | 11 | 466 | 0.03 | 0.45 | 0.90 | 55 | 1.7 | 1.4 | 72 |
|  |  | 578 | 0.03 | 0.50 |  |  | 1.7 |  | 72 |
| 53 | 12 | 472 | 0.04 | 0.42 | 0.88 | 60 | 2.5 | 2.1 | 70 |
|  |  | 579 | 0.04 | 0.48 |  |  | 2.5 |  | 70 |
| 54 | 13 | 466 | 0.03 | 0.36 | 0.71 | 55 | 1.8 | 1.3 | 74 |
|  |  | 576 | 0.03 | 0.51 |  |  | 1.8 |  | 74 |
| 55 | 14 | 476 | 0.04 | 0.43 | 0.81 | 60 | 1.8 | 1.9 | 69 |
|  |  | 587 | 0.04 | 0.53 |  |  | 1.8 |  | 69 |
| 56 | 15 | 480 | 0.03 | 0.39 | 0.80 | 60 | 1.8 | 1.9 | 73 |
|  |  | 590 | 0.03 | 0.49 |  |  | 1.8 |  | 73 |

TABLE 15

| Ex. No. | Compound No. | $\lambda$max (nm) | Initial color $\epsilon(0)$ | Color density $\epsilon(120)-\epsilon(0)$ | Yellow/blue ratio | Color-developing sensitivity (sec.) | Fading half-life $\tau^{1/2}$ (min.) | Light resistance $\Delta$YI | Remaining ratio (%) |
|---|---|---|---|---|---|---|---|---|---|
| 57 | 16 | 466 | 0.03 | 0.38 | 0.75 | 70 | 1.5 | 1.9 | 75 |
|  |  | 586 | 0.03 | 0.51 |  |  | 1.5 |  | 75 |
| 58 | 17 | 469 | 0.03 | 0.42 | 0.76 | 60 | 2.9 | 2.0 | 68 |
|  |  | 567 | 0.03 | 0.55 |  |  | 2.9 |  | 68 |
| 59 | 18 | 464 | 0.03 | 0.59 | 0.98 | 65 | 1.3 | 2.1 | 76 |
|  |  | 555 | 0.03 | 0.60 |  |  | 1.3 |  | 76 |
| 60 | 19 | 464 | 0.03 | 0.49 | 0.80 | 55 | 3.2 | 2.0 | 74 |
|  |  | 592 | 0.03 | 0.61 |  |  | 3.2 |  | 74 |
| 61 | 20 | 473 | 0.03 | 0.46 | 0.94 | 55 | 1.7 | 1.6 | 72 |
|  |  | 587 | 0.03 | 0.49 |  |  | 1.7 |  | 72 |
| 62 | 21 | 481 | 0.03 | 0.52 | 0.85 | 55 | 1.7 | 2.3 | 76 |
|  |  | 595 | 0.03 | 0.61 |  |  | 1.7 |  | 76 |
| 63 | 22 | 478 | 0.03 | 0.40 | 0.77 | 55 | 1.9 | 2.1 | 70 |
|  |  | 590 | 0.03 | 0.52 |  |  | 1.9 |  | 70 |
| 64 | 23 | 599 | 0.04 | 0.51 | 1.06 | 60 | 2.3 | 2.2 | 68 |
|  |  | 476 | 0.04 | 0.48 |  |  | 2.3 |  | 68 |
| 65 | 24 | 585 | 0.04 | 0.55 | 1.12 | 65 | 1.3 | 2.4 | 67 |
|  |  | 468 | 0.04 | 0.49 |  |  | 1.3 |  | 67 |

TABLE 15-continued

| Ex. No. | Compound No. | λmax (nm) | Initial color ε(0) | Color density ε(120)-ε(0) | Yellow/ blue ratio | Color-developing sensitivity (sec.) | Fading half-life τ½ (min.) | Light resistance ΔYI | Light resistance Remaining ratio (%) |
|---|---|---|---|---|---|---|---|---|---|
| 66 | 25 | 472 | 0.03 | 0.51 | 0.82 | 60 | 1.4 | 1.7 | 73 |
|  |  | 589 | 0.03 | 0.62 |  |  | 1.4 |  | 73 |
| 67 | 26 | 462 | 0.04 | 0.61 | 0.98 | 60 | 3.1 | 1.0 | 78 |
|  |  | 567 | 0.04 | 0.62 |  |  | 3.1 |  | 78 |
| 68 | 27 | 460 | 0.04 | 0.35 | 0.81 | 55 | 2.0 | 2.2 | 66 |
|  |  | 568 | 0.04 | 0.43 |  |  | 2.0 |  | 66 |
| 69 | 28 | 457 | 0.03 | 0.67 | 1.10 | 55 | 3.5 | 2.5 | 62 |
|  |  | 566 | 0.03 | 0.61 |  |  | 3.5 |  | 62 |
| 70 | 29 | 463 | 0.03 | 0.39 | 0.93 | 60 | 1.9 | 2.3 | 68 |
|  |  | 569 | 0.03 | 0.42 |  |  | 1.9 |  | 68 |
| 71 | 30 | 454 | 0.03 | 0.44 | 0.76 | 55 | 3.2 | 1.5 | 77 |
|  |  | 563 | 0.03 | 0.58 |  |  | 3.2 |  | 77 |

TABLE 16

| Ex. No. | Compound No. | λmax (nm) | Initial color ε(0) | Color density ε(120)-ε(0) | Yellow/ blue ratio | Color-developing sensitivity (sec.) | Fading half-life τ½ (min.) | Light resistance ΔYI | Light resistance Remaining ratio (%) |
|---|---|---|---|---|---|---|---|---|---|
| 72 | 31 | 472 | 0.04 | 0.67 | 1.00 | 70 | 1.4 | 1.2 | 73 |
|  |  | 588 | 0.04 | 0.67 |  |  | 1.4 |  | 73 |
| 73 | 32 | 462 | 0.03 | 0.33 | 0.66 | 60 | 2.5 | 1.9 | 69 |
|  |  | 578 | 0.03 | 0.50 |  |  | 2.5 |  | 69 |
| 74 | 33 | 470 | 0.04 | 0.55 | 1.00 | 65 | 1.2 | 1.2 | 73 |
|  |  | 590 | 0.04 | 0.55 |  |  | 1.2 |  | 73 |
| 75 | 34 | 458 | 0.03 | 0.60 | 1.20 | 60 | 2.0 | 2.0 | 70 |
|  |  | 568 | 0.03 | 0.50 |  |  | 2.0 |  | 70 |
| 76 | 35 | 466 | 0.03 | 0.58 | 1.00 | 60 | 1.8 | 2.0 | 70 |
|  |  | 580 | 0.03 | 0.58 |  |  | 1.8 |  | 70 |
| 77 | 36 | 468 | 0.04 | 0.62 | 1.03 | 65 | 2.0 | 1.4 | 70 |
|  |  | 578 | 0.04 | 0.60 |  |  | 2.0 |  | 70 |
| 78 | 37 | 468 | 0.04 | 0.61 | 1.03 | 65 | 2.1 | 1.4 | 68 |
|  |  | 578 | 0.04 | 0.59 |  |  | 2.1 |  | 68 |
| 79 | 38 | 468 | 0.03 | 0.35 | 0.73 | 60 | 1.1 | 1.3 | 74 |
|  |  | 570 | 0.03 | 0.48 |  |  | 1.1 |  | 74 |
| 80 | 39 | 462 | 0.03 | 0.55 | 1.00 | 55 | 2.5 | 2.1 | 66 |
|  |  | 572 | 0.03 | 0.55 |  |  | 2.5 |  | 66 |
| 81 | 40 | 468 | 0.04 | 0.64 | 1.00 | 65 | 2.2 | 1.6 | 68 |
|  |  | 578 | 0.04 | 0.64 |  |  | 2.2 |  | 68 |
| 82 | 41 | 474 | 0.04 | 0.39 | 0.80 | 60 | 1.4 | 1.8 | 72 |
|  |  | 592 | 0.04 | 0.49 |  |  | 1.4 |  | 72 |

For comparison, further, thin cured films of photochromic polymers were obtained in the same manner by using the compounds represented by the following formulas (A), (B), (C) and (D), and were evaluated for their properties (Comparative Examples 1 to 4). The results were as shown in Table 17.

(A)
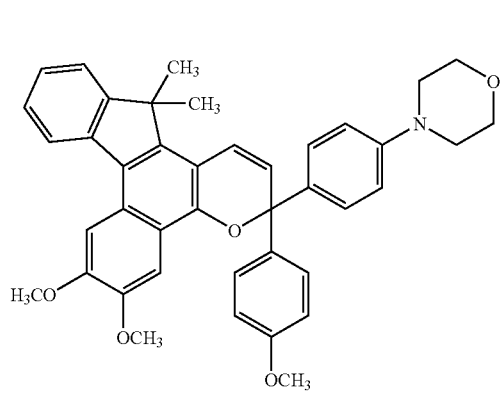

(B)
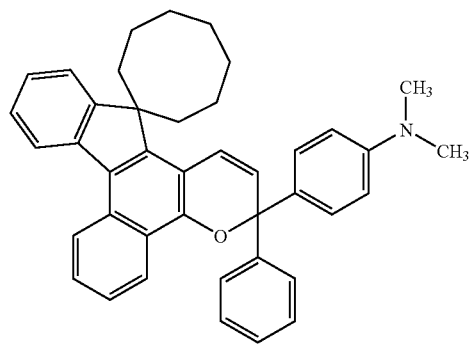

(C)
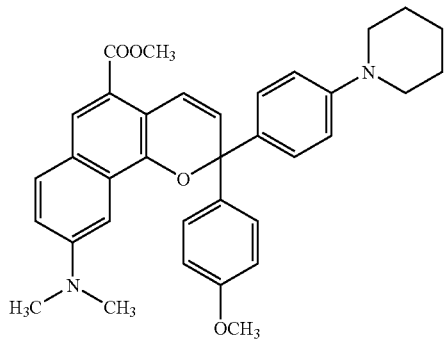

(D)
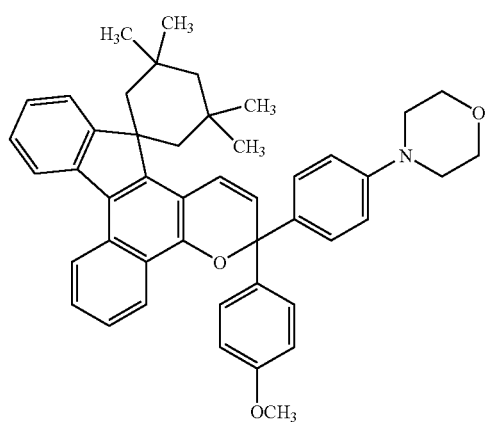

TABLE 17

| Comp Ex. No. | Compound No. | $\lambda$max (nm) | Initial color $\epsilon(0)$ | Color density $\epsilon(120)-\epsilon(0)$ | Yellow/ blue ratio | Color-developing sensitivity (sec.) | Fading half-life $\tau^{1/2}$ (min.) | Light resistance $\Delta$YI | Remaining ratio (%) |
|---|---|---|---|---|---|---|---|---|---|
| 1 | (A) | 474 | 0.03 | 0.56 | 1.00 | 55 | 7.0 | 3.0 | 50 |
|   |     | 592 | 0.03 | 0.56 |      |    | 7.0 |     | 50 |
| 2 | (B) | 486 | 0.03 | 0.32(sh) | 0.30 | 65 | 1.5 | 2.3 | 68 |
|   |     | 588 | 0.03 | 0.98 |      |    | 1.5 |     | 68 |
| 3 | (C) | 544 | 0.10 | 0.75 | — | 70 | 3.0 | 10.6 | 5 |
| 4 | (D) | 460 | 0.03 | 0.15(sh) | 0.29 | 90 | 1.9 | 1.9 | 72 |
|   |     | 570 | 0.03 | 0.51 |      |    | 1.9 |     | 72 |

*(sh) . . . sholder peak

Examples 83, 84 and Comparative Example 5

To 100 parts by weight of a polymerizable monomer comprising 2,2-bis(4-methacryloyloxydiethoxyphenyl)propane/polyethylene glycol diacrylate (average molecular weight of 742) at a ratio of 80 parts by weight/20 parts by weight ratio, there were added 0.04 parts by weight of the chromene compound obtained in Example 1 or in Example 9, and 1 part by weight of a perbutyl ND as a polymerization initiator, and the mixture was sufficiently mixed together to prepare photochromic polymerizable compositions.

The photochromic polymerizable compositions were poured into molds constituted by glass plates and a gasket of an ethylene/vinyl acetate copolymer, and were cast-polymerized. The polymerization was conducted by using an air furnace while gradually elevating the temperature from 30° C. up to 90° C. over 18 hours, and the temperature of 90° C. was maintained for 2 hours. After the polymerization, the polymers were taken out from the glass molds. The obtained polymers were evaluated for their photochromic properties by the same method as that of Example 42 but changing the irradiation time of the xenon Fade-meter into 100 hours in the acceleration testing to evaluate the light resistance. The results were as shown in Table 18.

For comparison, further, a photochromic polymer was obtained in the same manner by using a compound represented by the following formula (E). The results were as shown in Table 18 (Comparative Example 5).

Examples 85 and 86

Though the chromene compounds of Examples 1 to 41 exhibit neutral tints by themselves, the chromene compounds obtained in Examples 1 or 9 were mixed with the following compounds (F), (G) and with the above compounds (B), (D) at compositions shown in Table 19 to obtain more favorable neutral tints.

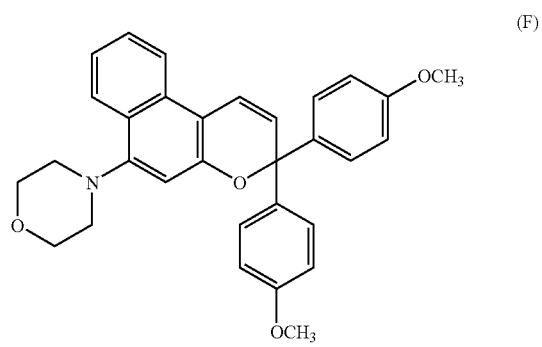

(F)

TABLE 18

(E)

| Ex. No. | Compound No. | λmax (nm) | Initial color ε(0) | Color density ε(120)-ε(0) | Yellow/ blue ratio | Color-developing sensitivity (sec.) | Fading half-life τ½ (min) | Light resistance YI | Light resistance Remaining ratio (%) |
|---|---|---|---|---|---|---|---|---|---|
| 83 | 1 | 456 | 0.02 | 0.56 | 0.78 | 60 | 1.6 | 3.0 | 80 |
|  |  | 582 | 0.02 | 0.72 |  |  | 1.6 |  | 80 |
| 84 | 9 | 454 | 0.03 | 0.62 | 0.85 | 60 | 1.8 | 4.0 | 73 |
|  |  | 584 | 0.03 | 0.73 |  |  | 1.8 |  | 73 |

| Comp. Ex. No. | Compound No. | λmax (nm) | Initial color ε(0) | Color density ε(120)-ε(0) | Yellow/ blue ratio | Color-developing sensitivity (sec.) | Fading half-life τ½ (min) | Light resistance YI | Light resistance Remaining ratio (%) |
|---|---|---|---|---|---|---|---|---|---|
| 5 | (E) | 454 | 0.23 | 0.64 | 0.98 | 55 | 6.9 | 32.0 | 65 |
|  |  | 564 | 0.38 | 0.65 |  |  | 6.9 |  | 65 |

-continued (G)

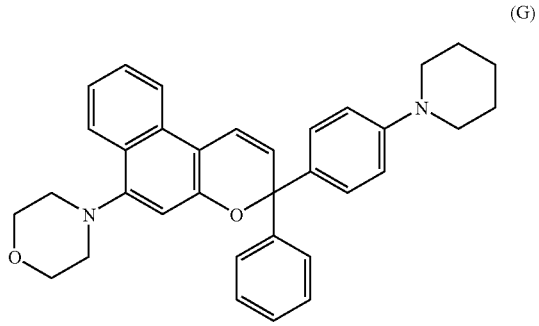

Further, polymer compositions were prepared in the same manner as in Example 42, and cured coatings were obtained. The obtained cured bodies were left to stand outdoors to develop colors, and the developed color tones were confirmed by naked eyes. The results were as shown in Table 19.

TABLE 19

| Ex. No. | Compound composition (wt. pts./100 wt. pts. of all polymerizable monomers) | | | | Developed color tone |
|---|---|---|---|---|---|
| | (F) | (G) | Ex. 1 | (D) | (E) | |
| 85 | 0.5 | 0.30 | 2.30 | 0.65 | 0.75 | grey |
| 86 | 1 | 0.50 | 2.00 | 0.40 | 0.3 | brown |

The photochromic polymers in Examples 42 to 84 using the chromene compounds of the present invention are superior to the photochromic polymers of Comparative Examples 1, 2, 3, 4 and 5 with respect to all of color-developing sensitivity, fading rate, and resistance of photochromic properties.

The invention claimed is:

1. A chromene compound having an indeno(2,1-f)naphtho(1,2-b)pyran structure represented by the following formula:

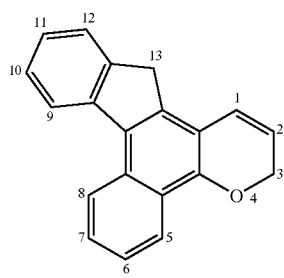

as a basic skeleton, wherein a substituted or unsubstituted aryl group or a substituted or unsubstituted heteroaryl group is bonded, as a substituent, to a carbon atom at the seventh position of the pyran structure;
an aliphatic monocyclic ring, which may have a lower alkyl group having not more than 4 carbon atoms as a substituent, is spiro-bonded to a carbon atom at the thirteenth position of the pyran structure; and
an alkoxy group or a p-alkylaminophenyl group having a Hamett number in a range of −0.49 to −0.2 is bonded to a carbon atom at the sixth position of the pyran structure.

2. A chromene compound represented by the following formula (4) according to claim 1,

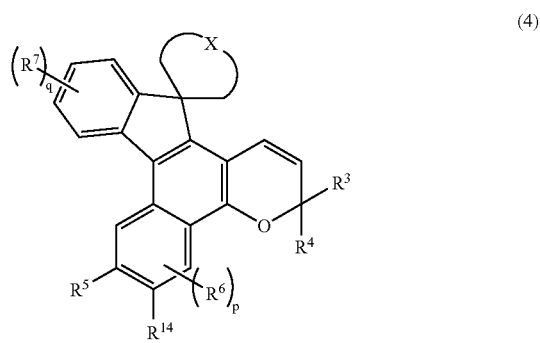

(4)

wherein p is an integer of 0 to 2,
q is an integer of 0 to 4,
$R^3$ and $R^4$ are independent from each other and are groups represented by the following formula (2) or (3), or are substituted or unsubstituted aryl groups, substituted or unsubstituted heteroaryl groups, or substituted or unsubstituted alkyl groups, or are bonded together to form an aliphatic hydrocarbon ring or an aromatic hydrocarbon ring,

(2)

(3)

wherein $R^{11}$ is a substituted or unsubstituted aryl group or a substituted or unsubstituted heteroaryl group, $R^{12}$ is a hydrogen atom, a substituted or unsubstituted alkyl group or a halogen atom, n is an integer of 1 to 3, $R^{13}$ is a substituted or unsubstituted aryl group or a substituted or unsubstituted heteroaryl group, m is an integer of 1 to 3,
$R^5$ is a substituted or unsubstituted aryl group or substituted or unsubstituted heteroaryl group;
$R^6$ and $R^7$ are independent from each other, and are unsubstituted alkyl groups, unsubstituted alkoxy groups, unsubstituted aralkoxy groups, unsubstituted or substituted amino groups, cyano groups, substituted or unsubstituted aryl groups, halogen atoms, unsubstituted aralkyl groups, substituted or unsubstituted heterocyclic groups having a nitrogen atom as a hetero atom and in which the nitrogen atom is bonded to a benzo ring, or condensed heterocyclic groups in which the heterocyclic group is condensed with an aromatic hydrocarbon ring or an aromatic heterocyclic ring, wherein when $R^6$ or $R^7$ are present in a plural number, $R^6$ present in a plural number or $R^7$ present in a plural number may be different from each other;
$R^{14}$ is a substituent bonded to the sixth position of the pyran structure and is an alkoxy group or a p-alkylaminophenyl group having a Hamett number in a range of −0.49 to −0.2; a group represented by the following formula (5) in the above formula (4),

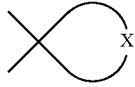 (5)

is an aliphatic monocyclic ring, which may have a lower alkyl group having not more than 4 carbon atoms as a substituent is spiro-bonded to a carbon atom at the thirteenth position of the pyran structure.

3. A photochromic composition containing a chromene compound described in claim 1.

4. A photochromic optical article having, as a constituent member, a high molecular molded body in which the chromene compound of claim 1 is dispersed.

5. An optical article having, as a constituent member, an optical base material of which at least one surface is wholly or partly coated with a high molecular film, said high molecular film containing the chromene compound of claim 1 dispersed therein.

* * * * *